(12) United States Patent
Tillberg et al.

(10) Patent No.: US 10,317,321 B2
(45) Date of Patent: *Jun. 11, 2019

(54) PROTEIN RETENTION EXPANSION MICROSCOPY

(71) Applicant: Massachusetts Institute of Technology, Cambridge, MA (US)

(72) Inventors: Paul Warren Tillberg, Cambridge, MA (US); Fei Chen, Cambridge, MA (US); Edward Stuart Boyden, Chestnut Hill, MA (US); Chih-Chieh Yu, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 257 days.

This patent is subject to a terminal disclaimer.

(21) Appl. No.: 15/229,545

(22) Filed: Aug. 5, 2016

(65) Prior Publication Data

US 2017/0089811 A1 Mar. 30, 2017

Related U.S. Application Data

(60) Provisional application No. 62/202,423, filed on Aug. 7, 2015.

(51) Int. Cl.
| | | |
|---|---|---|
| G01N 1/30 | (2006.01) | |
| G01N 1/36 | (2006.01) | |
| G01N 33/58 | (2006.01) | |
| G01N 33/68 | (2006.01) | |

(52) U.S. Cl.
CPC ............ *G01N 1/30* (2013.01); *G01N 1/36* (2013.01); *G01N 33/582* (2013.01); *G01N 33/6803* (2013.01); *G01N 2001/302* (2013.01); *G01N 2001/307* (2013.01); *G01N 2333/95* (2013.01)

(58) Field of Classification Search
None
See application file for complete search history.

(56) References Cited

U.S. PATENT DOCUMENTS

| | | | |
|---|---|---|---|
| 5,952,232 | A | 9/1999 | Rothman |
| 6,107,081 | A | 8/2000 | Feedback et al. |
| 6,271,278 | B1 | 8/2001 | Park et al. |
| 6,287,870 | B1 | 9/2001 | Wardlaw |
| 2002/0176880 | A1 | 11/2002 | Cruise et al. |
| 2003/0120231 | A1 | 6/2003 | Wang |
| 2004/0248326 | A1 | 12/2004 | Ziaie et al. |
| 2005/0034990 | A1 | 2/2005 | Crooks et al. |
| 2005/0090016 | A1 | 4/2005 | Rich et al. |
| 2005/0169962 | A1 | 8/2005 | Bhatia et al. |
| 2005/0196702 | A1 | 9/2005 | Bryant et al. |
| 2006/0000767 | A1 | 1/2006 | Trauger |
| 2006/0003356 | A1 | 1/2006 | Shaw et al. |
| 2006/0110760 | A1 | 5/2006 | Kim et al. |
| 2006/0115146 | A1 | 6/2006 | Ogura et al. |
| 2006/0165912 | A1 | 7/2006 | Koberstein et al. |
| 2007/0023942 | A1 | 2/2007 | Andino et al. |
| 2007/0134902 | A1 | 6/2007 | Bertino et al. |
| 2008/0261834 | A1 | 10/2008 | Simon |
| 2008/0286360 | A1 | 11/2008 | Shoichet et al. |
| 2009/0011141 | A1 | 1/2009 | Carter et al. |
| 2009/0011420 | A1 | 1/2009 | Barron et al. |
| 2009/0096133 | A1 | 4/2009 | Doyle et al. |
| 2009/0191627 | A1 | 7/2009 | Fadeev et al. |
| 2009/0241681 | A1 | 10/2009 | Machauf |
| 2010/0041128 | A1 | 2/2010 | Banes et al. |
| 2010/0055161 | A1 | 3/2010 | Ahn |
| 2010/0056445 | A1 | 3/2010 | Sharma et al. |
| 2010/0068725 | A1 | 3/2010 | Armbrumster et al. |
| 2010/0096334 | A1 | 4/2010 | Edmiston |
| 2010/0119755 | A1 | 5/2010 | Chung et al. |
| 2011/0070604 | A1 | 3/2011 | Gimzewski et al. |
| 2011/0009171 | A1 | 4/2011 | Weiss |
| 2011/0087315 | A1 | 4/2011 | Richardson-Burns et al. |
| 2011/0091922 | A1 | 4/2011 | Krishnan et al. |
| 2011/0291357 | A1 | 12/2011 | Boyle |
| 2012/0184670 | A1 | 7/2012 | Kobayashi et al. |
| 2012/0220478 | A1 | 8/2012 | Shaffer |
| 2012/0251527 | A1 | 10/2012 | Reiser |
| 2012/0310223 | A1 | 12/2012 | Knox et al. |
| 2013/0045503 | A1 | 2/2013 | Miyawaki et al. |

(Continued)

FOREIGN PATENT DOCUMENTS

| | | |
|---|---|---|
| JP | 2009191125 | 8/2009 |
| JP | 2014005231 | 1/2014 |

(Continued)

OTHER PUBLICATIONS

Chen, F., Tillberg, P. W. & Boyden, E. S. Expansion microscopy. Science (80-.). 347, 543-548 (2015).
Laemmli, U. K. Cleavage of structural proteins during the assembly of the head of bacteriophage T4. Nature 227, 680-685 (1970).
Hunt, et al., High temperature antigen retrieval and loss of nuclear morphology: a comparison of microwave\rand autoclave techniques. J. Clin. Pathol. 49, 767-770 (1996).
Jekel, P. A., Weijer, W. J. & Beintema, J. J. Use of endoproteinase Lys-C from Lysobacter enzymogenes in protein sequence analysis. Anal. Biochem. 134, 347-354 (1983).
Wu, C. C., MacCoss, M. J., Howell, K. E. & Yates, J. R. A method for the comprehensive proteomic analysis of membrane proteins. Nat. Biotechnol. 21, 532-8 (2003).

(Continued)

*Primary Examiner* — Changhwa J Cheu
(74) *Attorney, Agent, or Firm* — Elmore Patent Law Group, P.C.; Joseph Zucchero; Carolyn Elmore

(57) ABSTRACT

The invention provides a method termed protein retention ExM (proExM), in which proteins, rather than labels, are anchored to the swellable gel, using a cross-linking molecule. This proExM strategy can be used to perform nanoscale imaging of immunostained cells and tissues as well as samples expressing various FPs as fluorescent signals from genetically encoded fluorescent proteins and/or conventional fluorescently labeled secondary antibodies and streptavidin that are directly anchored to the gel are preserved even when subjected to the nonspecific proteolytic digestion.

27 Claims, 31 Drawing Sheets

(56) References Cited

U.S. PATENT DOCUMENTS

| | | |
|---|---|---|
| 2013/0203605 A1 | 8/2013 | Shendure et al. |
| 2014/0087139 A1 | 3/2014 | Rowley et al. |
| 2014/0193651 A1 | 7/2014 | Kharlampieva et al. |
| 2016/0116384 A1 | 4/2016 | Chen et al. |
| 2016/0252528 A1 | 9/2016 | Sangarlingham et al. |
| 2016/0304952 A1 | 10/2016 | Boyden et al. |
| 2016/0305856 A1 | 10/2016 | Boyden et al. |
| 2017/0067096 A1 | 3/2017 | Wassie et al. |
| 2017/0081489 A1 | 3/2017 | Rodriques et al. |
| 2017/0089811 A1 | 3/2017 | Tillberg et al. |

FOREIGN PATENT DOCUMENTS

| | | |
|---|---|---|
| WO | 200008212 | 2/2000 |
| WO | 2012142664 | 10/2012 |
| WO | 2014025392 A1 | 2/2014 |
| WO | 2014152984 | 9/2014 |
| WO | 2015127183 | 8/2015 |
| WO | 2015127183 A2 | 8/2015 |
| WO | 2017027367 | 2/2017 |
| WO | 2017027368 | 2/2017 |

OTHER PUBLICATIONS

Sniegowski, J. A., Phail, M. E. & Wachter, R. M. Maturation efficiency, trypsin sensitivity, and optical properties of Arg96, Glu222, and Gly67 variants of green fluorescent protein. Biochem. Biophys. Res. Commun. 332, 657-63 (2005).

Bokman, S. H. & Ward, W. W. Renaturation of Aequorea gree- fluorescent protein. Biochem. Biophys. Res. Commun. 101, 1372-80 (1981).

Seneviratne, U. et al. S-nitrosation of proteins relevant to Alzheimer's disease during early stages of neurodegeneration. Proc. Natl. Acad. Sci. U. S. A. 1521318113—(2016). doi:10.1073/pnas.1521318113.

Huang, B., Jones, S. A., Brandenburg, B. & Zhuang, X. Whole-cell 3D STORM reveals interactions between cellular structures with nanometer-scale resolution. Nat. Methods 5, 1047-1052 (2008).

Rego, E. H. et al. Nonlinear structured-illumination microscopy with a photoswitchable protein reveals cellular structures at 50-nm resolution. Proc. Natl. Acad. Sci. U. S. A. 109, E135-43 (2012).

Bates, M., Huang, B., Dempsey, G. T. & Zhuang, X. Multicolor super-resolution imaging with photo-switchable fluorescent probes. Science 317, 1749-1753 (2007).

Bossi, M. et al. Multicolor far-field fluorescence nanoscopy through isolated detection of distinct molecular species. Nano Lett. 8, 2463-8 (2008).

Cai, D., Cohen, K. B., Luo, T., Lichtman, J. W. & Sanes, J. R. Improved tools for the Brainbow toolbox. Nat. Methods 10, 540-7 (2013).

Livet, J. et al. Transgenic strategies for combinatorial expression of fluorescent proteins in the nervous system. Nature 450, 56-62 (2007).

Schnell, U., Dijk, F., Sjollema, K. A. & Giepmans, B. N. G. Immunolabeling artifacts and the need for live-cell imaging. Nat. Methods 9, 152-158 (2012).

Hackstadt, T. Steric hindrance of antibody binding to surface proteins of Coxiella burnetti by phase I lipopolysaccharide. Infect Immun 56, 802-807 (1988).

Jimenez, N. & Post, J. A. A Novel Approach for Intracellular 3D Immuno-Labeling for Electron Tomography. Traffic 13, 926-933 (2012).

Randall, K. J. & Pearse, G. A dual-label technique for the immunohistochemical demonstration of T-lymphocyte subsets in formalin-fixed, paraffin-embedded rat lymphoid tissue. Toxicol. Pathol. 36, 795-804 (2008).

Kakimoto, K., Takekoshi, S., Miyajima, K. & Osamura, R. Y. Hypothesis for the mechanism for heat-induced antigen retrieval occurring on fresh frozen sections without formalin-fixation in immunohistochemistry. J Mol Histol 39, 389-399 (2008).

Wachter, R. M. & James Remington, S. Sensitivity of the yellow variant of green fluorescent protein to halides and nitrate. Curr. Biol. 9, R628-R629 (1999).

Carpenter, A. E. et al. CellProfiler: image analysis software for identifying and quantifying cell phenotypes. Genome Biol. 7, R100 (2006).

Lowe, D. G. Distinctive Image Features from Scale-Invariant Keypoints. Int. J. Comput. Vis. 60, 91-110 (2004).

Vedaldi, A. & Fulkerson, B. Vlfeat. In Proc. Int. Conf. Multimed.— MM '10 1469 (ACM Press, 2010). doi:10.1145/1873951.1874249.

English, B. P. & Singer, R. H. A three-camera imaging microscope for high-speed single-molecule tracking and super-resolution imaging in living cells. in SPIE Nanosci. + Eng. (Mohseni, H., Agahi, M. H. & Razeghi, M.) 955008 (International Society for Optics and Photonics, 2015). doi:10.1117/12.2190246.

Edelstein, A., Amodaj, N., Hoover, K., Vale, R. & Stuurman, N. Computer control of microscopes using µManager. Curr. Protoc. Mol. Biol. Chapter 14, Unit14.20 (2010).

Dedecker, P., Duwé, S., Neely, R. K. & Zhang, J. Localizer: fast, accurate, open-source, and modular software package for super-resolution microscopy. J. Biomed. Opt. 17, 126008 (2012).

Mortensen, K. I., Churchman, L. S., Spudich, J. A. & Flyvbjerg, H. Optimized localization analysis for single-molecule tracking and super-resolution microscopy. Nat. Methods 7, 377-81 (2010).

Al, H., Shaner, N. C., Cheng, Z., Tsien, R. Y. & Campbell, R. E. Exploration of new chromophore structures leads to the identification of improved blue fluorescent proteins. Biochemistry 46, 5904-10 (2007).

Subach, O. M., Cranfill, P. J., Davidson, M. W. & Verkhusha, V. V. An Enhanced Monomeric Blue Fluorescent Protein with the High Chemical Stability of the Chromophore. PLoS One 6, e28674 (2011).

Goedhardt, J. et al. Structure-guided evolution of cyan fluorescent proteins towards a quantum yield of 93%. Nat. Commun. 3, 751 (2012).

Markwardt, M. L. et al. An improved cerulean fluorescent protein with enhanced brightness and reduced reversible photoswitching. PLoS One 6, e17896 (2011).

Heim, R., Prasher, D. C. & Tsien, R. Y. Wavelength mutations and posttranslational autoxidation of green fluorescent protein. Proc. Natl. Acad. Sci. U. S. A. 91, 12501-4 (1994).

Heim, R. & Tsien, R. Y. Engineering green fluorescent protein for improved brightness, longer wavelengths and fluorescence resonance energy transfer. Curr. Biol. 6, 178-82 (1996).

Rose, R. C. & Bode, A. M. Ocular ascorbate transport and metabolism. Comp. Biochem. Physiol. A. Comp. Physiol. 100, 273-85 (1991).

Cubitt, A. B., Woollenweber, L. A. & Heim, R. Understanding structure-function relationships in the Aequorea victoria green fluorescent protein. Methods Cell Biol. 58, 19-30 (1999).

Cormack, B. P., Valdivia, R. H. & Falkow, S. FACS-optimized mutants of the green fluorescent protein (GFP). Gene 173, 33-8 (1996).

Lam, A. J. et al. Improving FRET dynamic range with bright green and red fluorescent proteins. Nat. Methods 9, 1005-12 (2012).

Ormo, M. et al. Crystal structure of the Aequorea victoria green fluorescent protein. Science 273, 1392-5 (1996).

Nagai, T. et al. A variant of yellow fluorescent protein with fast and efficient maturation for cell-biological applications. Nat. Biotechnol. 20, 87-90 (2002).

Griesbeck, O., Baird, G. S., Campbell, R. E., Zacharias, D. A. & Tsien, R. Y. Reducing the environmental sensitivity of yellow fluorescent protein. Mechanism and applications. J. Biol. Chem. 276, 29188-94 (2001).

Shaner, N. C. et al. Improving the photostability of bright monomeric orange and red fluorescent proteins. Nat. Methods 5, 545-51 (2008).

Shcherbakova, D. M., Hink, M. A., Joosen, L., Gadella, T. W. J. & Verkhusha, V. V. An orange fluorescent protein with a large Stokes shift for single-excitation multicolor FCCS and FRET imaging. J. Am. Chem. Soc. 134, 7913-23 (2012).

(56) References Cited

OTHER PUBLICATIONS

Shaner, N. C. et al. Improved monomeric red, orange and yellow fluorescent proteins derived from *Discosoma* sp. red fluorescent protein. Nat. Biotechnol. 22, 1567-72 (2004).
Shcherbo, D. et al. Far-red fluorescent tags for protein imaging in living tissues. Biochem. J. 418, 567-74 (2009).
Chu, J. et al. Non-invasive intravital imaging of cellular differentiation with a bright red-excitable fluorescent protein. Nat. Methods 11, 572-8 (2014).
Filonov, G. S. et al. Bright and stable near-infrared fluorescent protein for in vivo imaging. Nat. Biotechnol. 29, 757-61 (2011).
Gurskaya, N. G. et al. Engineering of a monomeric green-to-red photoactivatable fluorescent protein induced by blue light. Nat. Biotechnol. 24, 461-5 (2006).
McKinney, S. A., Murphy, C. S., Hazelwood, K. L., Davidson, M. W. & Looger, L. L. A bright and photostable photoconvertible fluorescent protein. Nat. Methods 6, 131-3 (2009).
Habuchi, S., Tsutsui, H., Kochaniak, A. B., Miyawaki, A. & van Oijen, A. M. mKikGR, a monomeric photoswitchable fluorescent protein. PLoS One 3, e3944 (2008).
Subach F. V, Patterson, G. H., Renz, M., Lippincott-Schwartz, J. & Verkhusha, V. V. Bright monomeric photoactivatable red fluorescent protein for two-color super-resolution sptPALM of live cells. J. Am. Chem. Soc. 132, 6481-91 (2010).
Chen, F., et al., "Supplementary Material for Expansion Microscopy," Science, vol. 347, No. 6221, pp. 1-18, Jan. 2015.
Nilsson, M., et al., "RNA-Templated DNA Ligation for Transcript Analysis," Nucleic Acids Research, 29(2): pp. 578-581 (2001).
Park, Y., et al., Detection of Hepatitis C Virus RNA Using Ligation-Dependent Polymerase Chain Reaction in Formalin-Fixed, Paraffin-Embedded Liver Tissues, American Journal of Pathology, 149(5): pp. 1485-1491 (1996).
Nagre, R.D., et al., "Thermosaline Resistant Acrylamide-Based Polyelectrolyte as Filtration Control Additive in Aqueous-Based Mud. Petroleum and Coal," vol. 56(3), pp. 222-230, 2014.
Lee, et al., "Highly Multiplexed Subcelluar RNA Sequencing In Situ," Science Express, pp. 1-6 (Feb. 2014).
Kaur, et al., Biochemistry 45, pp. 7347-7355 (2006).
Cai, et al., Nat Meth 10, pp. 540-547 (2013).
Zimmerman, et al., Adapting the stretched sample method from tissue profiling to imaging, Proteomics, 8, (2008), p. 3809-3815. (Year: 2008).
Chang, et al., Iterative expansion microscopy, Nature Methods, 14(6), (2017), p. 593-599, and supplemental info (4 pages, 11 pages total) (Year: 2017).
Chen, F., et al., "Expansion Microscopy," Science, vol. 347, No. 6221, p. 543, Jan. 2015.
Chen, F., et al., "Nanoscale Imaging of RNA with Expansion Microscopy," HHS Public Access Author Manuscript, vol. 13(8): pp. 679-684 (Aug. 2016).
Chen, F., et al., "Supplementary Material for Expansion Microscopy," Science, vol. 347, No. 6221, pp. 543-548, Jan. 2015.
Reinhart-King, C., et al., "The Dynamics and Mechanics of Endothelial Cell Spreading," Biophysical Journal, vol. 89, pp. 676-689, Jul. 2005.
Van Vliet, et al., The Biomechanics Toolbox: Experimental Approaches for Living Cells and Biomolecules, Acta Materialia 51: pp. 5881-5905, Aug. 23, 2003, [online], retrieved from the Internet, Oct. 23, 2015.
Batish, M., et al., "Neuronal mRNAs Travel Singly into Dendrites," PNAS, vol. 109(12): pp. 4645-4650 (2012).
Beliveau, B., et al. "Versatile design and synthesis platform for visualizing genomes with Oligopaint FISH probes," PNAS, vol. 109(52): pfa. 21301-21306 (2012).
Bruchez, M., et al., "Semiconductor nanocrystals as fluorescent biological labels," Science, vol. 281, pp. 2013-2016 (1998).
Buckley, P., et al., "Cytoplasmic Intron Sequence-Retaining Transcripts Can Be Dendritically Targeted via ID Element Retrotransposons," Neuron, vol. 69, pp. 877-884 (2011).

Buxbaum, A., et al., Single-Actin mRNA Detection in Neurons Reveals a Mechanism for Regulating Its Translatability, Science, vol. 343, pp. 419-422 (2014).
Cabili, M., et al., "Localization and abundance analysis of human lncRNAs at single-cell and single-molecule resolution," Genome Biology, vol. 16(20) (2015).
Cajigas, I. et al., "The local transcriptome in the synaptic neuropil revealed by deep sequencing and high-resolution imaging," Neuron 74, pp. 453-466 (2012).
Chen, K., et al., "Spatially resolved, highly multiplexed RNA profiling in single cells," Science. vol. 348(6233), (2015). aaa6090-aaa6090 (2015).
Choi, H., et al., "Next-Generation in Situ Hybridization Chain Reaction: Higher Gain, Lower Cost, Greater Durability," ACS Nano 8(5): pp. 4284-4294 (2014).
Choi, H. et al., "Programmable in situ amplification for multiplexed imaging of mRNA expression," Nature Biotechnology, 28(11): pp. 1208-1212 (2010).
Chozinski, T., et al., "Expansion microscopy with conventional antibodies and fluorescent proteins," . Nature Methods, vol. 13(6): pp. 485-491 (2016).
Clemson, C., et al., "An architectural role for a nuclear noncoding RNA: NEAT1 RNA is essential for the structure of paraspeckles," Molecular Cell, 33,717-26 (2009).
Engreitz, J., et al. "The Xist lncRNA exploits three-dimensional genome architecture to spread across the X chromosome," Science 341, 1237973 (2013).
Femino, A., et al., "Visualization of Single RNA Transcripts in Situ," Science, vol. 280; pp. 585-590 (1998).
Feng, G., et al., "Imaging neuronal subsets in transgenic mice expressing multiple spectral variants of GFP," Neuron 28, pp. 41-51 (2000).
Fouz, M., et al., "Bright Fluorescent Nanotags from Bottlebrush Polymers with DNA-Tipped Bristles," ACS Central Science, vol. 1, pp. 431-438 (2015).
Freifeld, et al., Expansion Microscopy of Zebrafish for Neuroscience and Developmental Biology Studies, PNAS, pp. E10799-E10808 (2017).
Huisken, J., et al., "Optical Sectioning Deep Inside Live Embryos by Selective Plane Illumination Microscopy," Science. vol. 305, 1007-1009 (2004).
Jung, H., et al., "Axonal mRNA localization and local protein synthesis in nervous system assembly, maintenance and repair," Nat. Rev. Neurosci., vol. 13(5): pp. 308-324 (2012).
Ke, R., et al., "In situ sequencing for RNA analysis in preserved tissue and cells," Nature Methods, vol. 10(9): pp. 857-860 (2013).
Lee, J., et al., "Highly Multiplexed Subcellular RNA Sequencing in Situ," Science, vol. 343, pp. 1360-1363 (2014).
Lein, E., et al. "Genome-wide atlas of gene expression in the adult mouse brain," Nature, vol. 445, 168-76 (2007).
Levsky, J., et al., "Fluorescence in situ hybridization: past, present and future," Journal of Cell Science, 116, 2833-2838 (2003).
Lieberman-Aiden, E., et al., "Comprehensive mapping of long-range interactions reveals folding principles of the human genome," Science 326, pp. 289-293 (2009).
Lubeck, E., et al., "Single-cell in situ RNA profiling by sequential hybridization," Nature Methods, vol. 11(4): pp. 360-361 (2014).
Lubeck, E., et al., "Single-cell systems biology by super-resolution imaging and combinatorial labeling," Nature Methods, vol. 9, 743-8 (2012).
Mito, M., et al., "Simultaneous multicolor detection of RNA and proteins using super-resolution microscopy," Methods (2015). doi:10. 1016/j.ymeth.2015.11.007.
Panning, B., et al., "X chromosome Inactivation is Mediated by by Xist RNA stabilization," Cell. vol. 90, 907-16 (1997).
Plath, K., et al., "Xist RNA and the mechanism of X chromosome inactivation," Annu. Rev. Genet. 36, 233-78 (2002).
Raj, A., et al., "Detection of individual endogenous RNA transcripts in situ using multiple singly labeled probes," Methods in Enzymology, vol. 472, pp. 365-386, (Elsevier Inc., 2010).
Raj, A., et al., Imaging individual mRNA molecules using multiple singly labeled probes. Nat. Methods 5(10: pp. 877-879 (2008).

(56) References Cited

OTHER PUBLICATIONS

Schindelin J., et al., "Fiji: an open-source platform for biological-image analysis," Nature Methods, vol. 9, pp. 676-682 (2012).
Shah, S., et al., "Single-molecule RNA detection at depth via hybridization chain reaction and tissue hydrogel embedding and clearing," Development in Review, (2016).
Steward, O., et al., "Compartmentalized synthesis and degradation of proteins in neurons," Neuron, vol. 40, pp. 347-359 (2003).
Steward, O., et al., Synaptic activation causes the mRNA for the leg Arc to localize selectively near activated postsynaptic sites on dendrites. Neuron, vol. 21, pp. 741-751 (1998).
Thevenaz, P., et al., "A pyramid approach to subpixel registration based on intensity," IEEE Trans. Image Process. 7, 27-41 (1988).
Tillberg, P., et al., "Protein-Retention Expansion Microscopy of Cells and Tissues Labeled Using Standard Fluorescent Proteins and Antibodies," Nature Biotechnology vol. 34(9): pp. 987-995 (2016).
Wang, F., et al., "RNAscope: A novel in situ RNA analysis platform for formalin-fixed, paraffin-embedded tissues," Journal of Molecular Diagnostics, vol. 14(1): pp. 22-29 (2012).
Zhang, D., et al., "Dynamic DNA nanotechnology using strand-displacement reactions," Nature Chemistry, vol. 3, pp. 103-113 (2011).
Strack, R., "Imaging: Bigger is better for super-resolution," Nature Methods, vol. 12(3), pp. 169-169 (2015).
Cao, W., "DNA Ligases and Ligase-Based Technologies," Clinical and Applied Immunology Reviews 2, pp. 33-43 (2001).

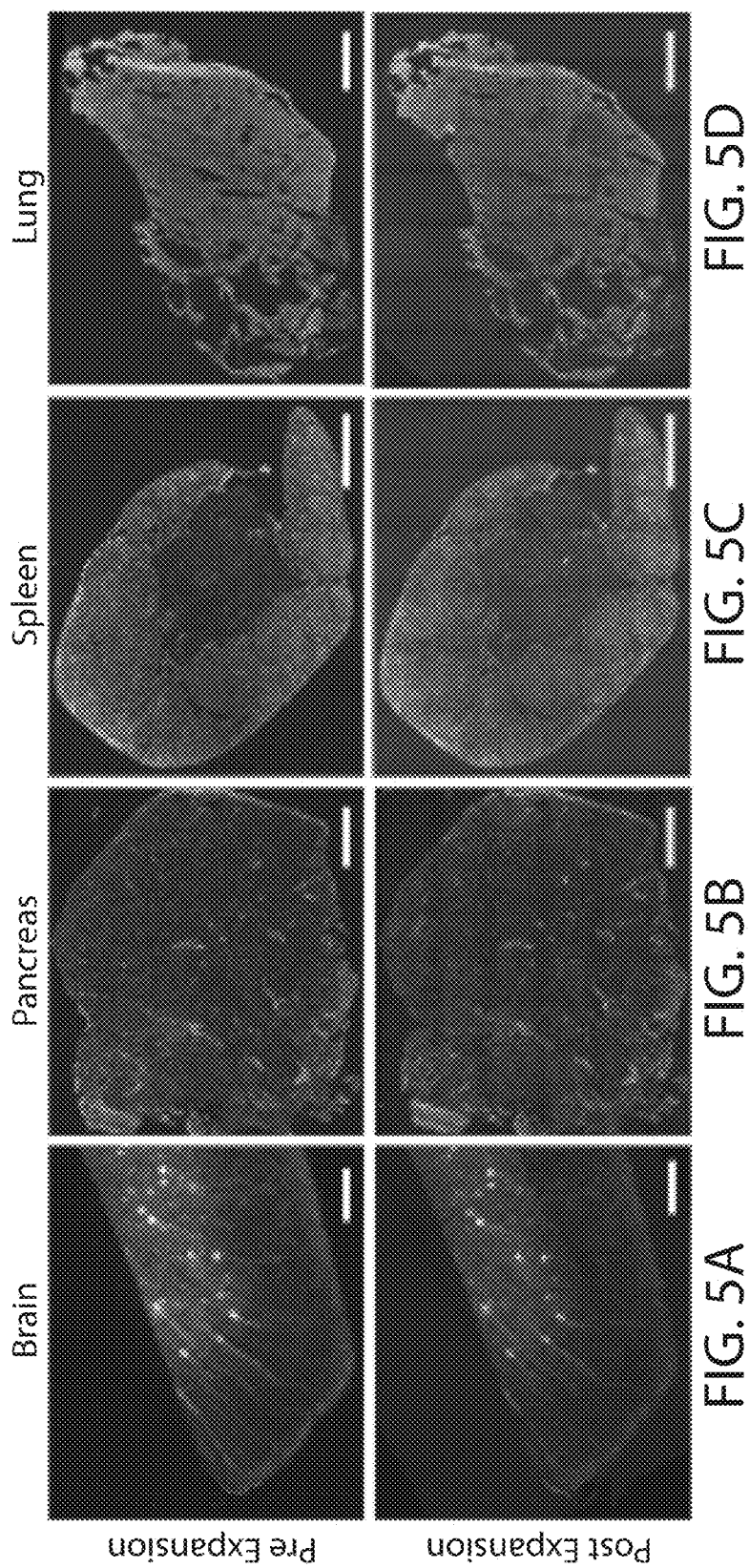

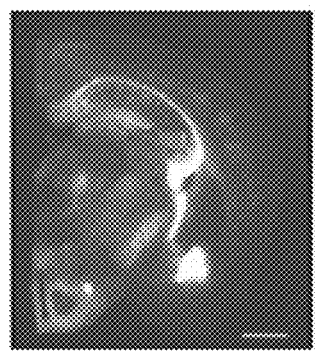
FIG. 8A
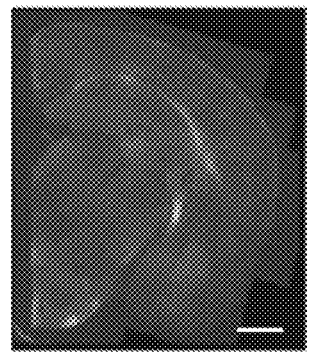
FIG. 8B
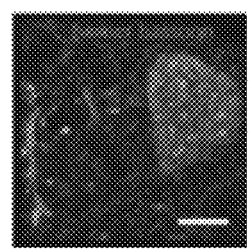
FIG. 8C
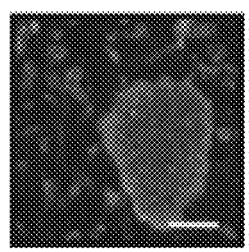
FIG. 8D
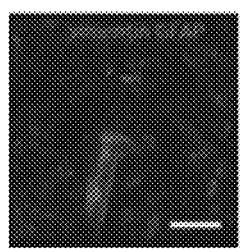
FIG. 8E
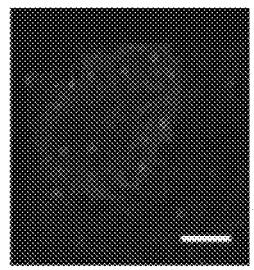
FIG. 8F(i)
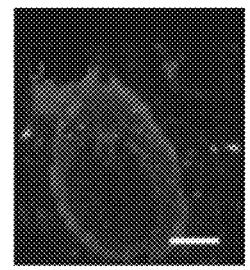
FIG. 8F(ii)
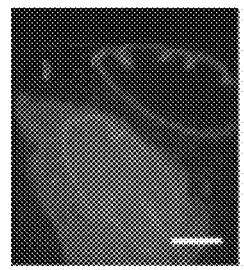
FIG. 8F(iii)
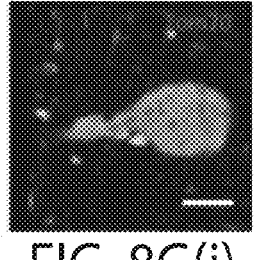
FIG. 8G(i)
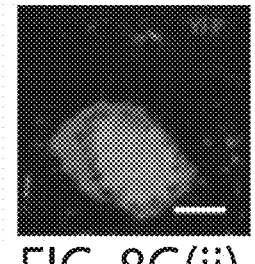
FIG. 8G(ii)
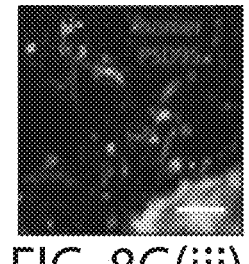
FIG. 8G(iii)
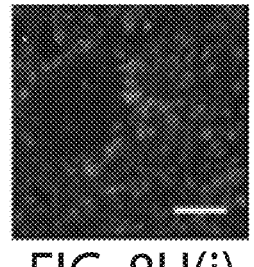
FIG. 8H(i)
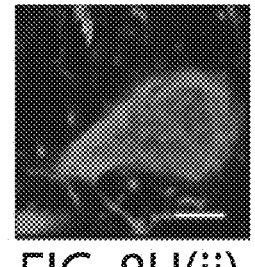
FIG. 8H(ii)
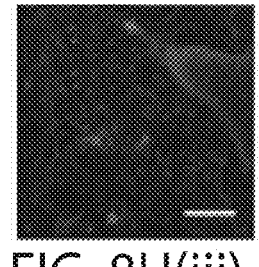
FIG. 8H(iii)

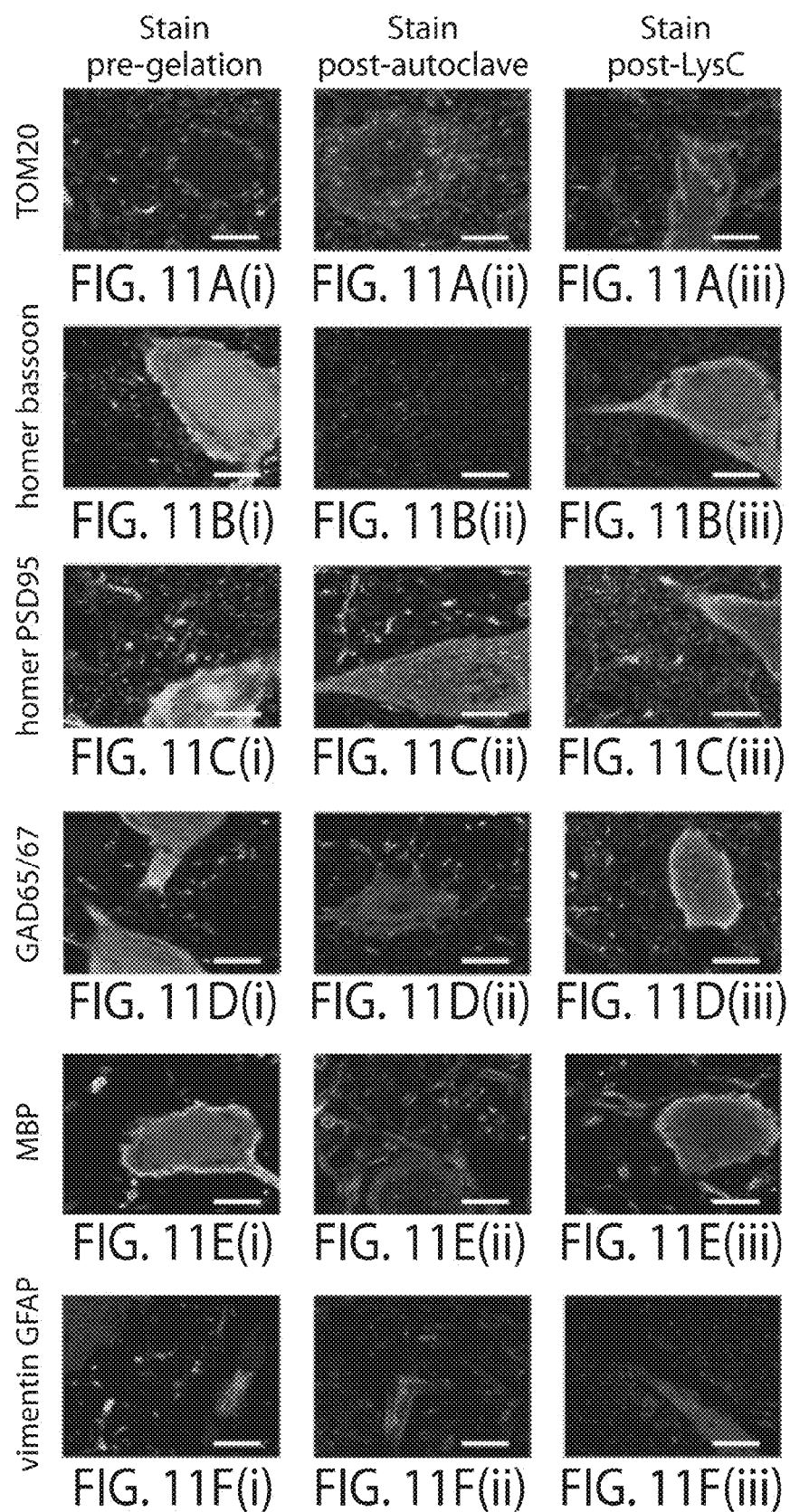

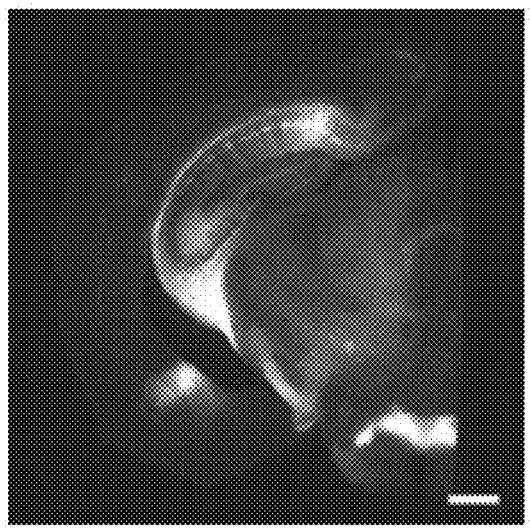 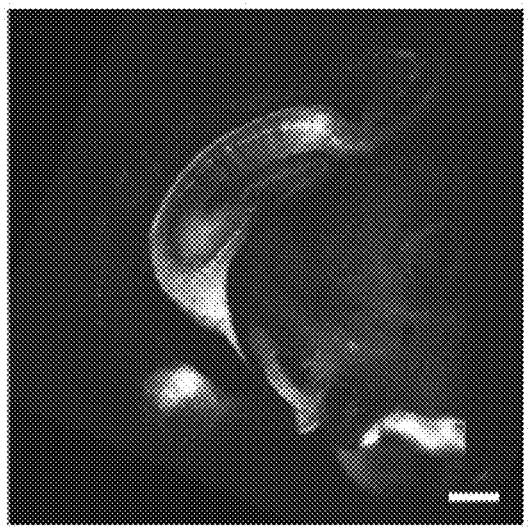
FIG. 15A  FIG. 15B
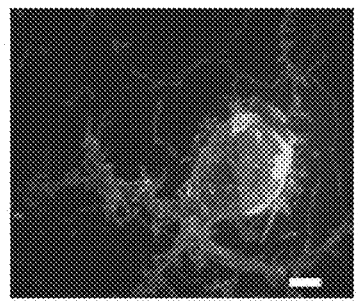 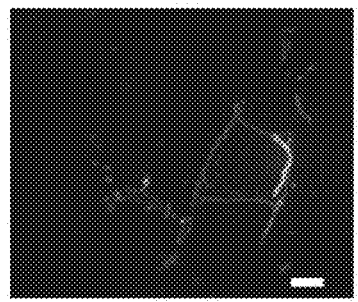 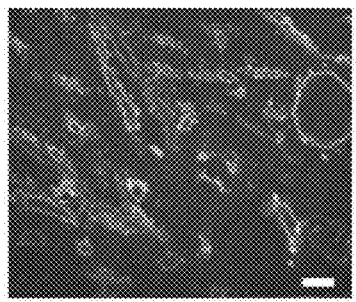
FIG. 15C  FIG. 15D  FIG. 15E

PROTEIN RETENTION EXPANSION MICROSCOPY

RELATED APPLICATIONS

This application claims the benefit of U.S. Provisional Application Ser. No. 62/202,423, filed Aug. 7, 2015, the contents of which are incorporated herein by reference in its entirety.

GOVERNMENT SUPPORT

This invention was made with government support under NYSCF-R-NI10 awarded by Hertz Foundation, NYSCF, NSF, and the Rehabilitation Institute of Chicago and 1-U01-MH106011 awarded by NIH and Cargill Fund Bioengineering Fund. The government has certain rights in the invention.

BACKGROUND

Expansion microscopy (ExM) enables imaging of thick preserved specimens with ~70 nm lateral resolution. Using ExM the optical diffraction limit is circumvented by physically expanding a biological specimen before imaging, thus bringing sub-diffraction limited structures into the size range viewable by a conventional diffraction-limited microscope. ExM can image biological specimens at the voxel rates of a diffraction limited microscope, but with the voxel sizes of a super-resolution microscope. Expanded samples are transparent, and index-matched to water, as the expanded material is >99% water. The original ExM protocol worked by labeling biomolecules of interest with a gel-anchorable fluorophore. Then, a swellable polyelectrolyte gel was synthesized in the sample, so that it incorporated the labels. Finally, the sample was treated with a nonspecific protease to homogenize its mechanical properties, followed by dialysis in water to mediate uniform physical expansion of the polymer-specimen composite. All of the chemicals required for ExM can be purchased except for the gel-anchorable label, which requires custom synthesis and raises the barrier for researchers to adopt the method. Another drawback of the ExM protocol is that genetically encoded fluorophores cannot be imaged without antibody labeling. Additionally, ExM was unable to retain native proteins in the gel and used custom made reagents not widely available. Thus, it would be desirable to leverage ExM to devise new methods for in situ retention and imaging of proteins within a sample.

SUMMARY OF THE INVENTION

The invention provides a method termed protein retention ExM (proExM), in which proteins, rather than labels, are anchored to the swellable gel, using a cross-linking molecule. This proExM strategy can be used to perform nanoscale imaging of immunostained cells and tissues as well as samples expressing various FPs as fluorescent signals from genetically encoded fluorescent proteins and/or conventional fluorescently labeled secondary antibodies and streptavidin that are directly anchored to the gel are preserved even when subjected to the nonspecific proteolytic digestion.

In one embodiment, the invention provides a method for the retention and imaging of proteins of a sample of interest comprising the steps conjugating proteins within the sample with a bifunctional crosslinker; embedding the sample in a swellable material wherein proteins within the sample are anchored to the swellable material; subjecting the sample to digestion; swelling the swellable material to form an expanded sample; and imagining the sample of interest.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 8a through FIG. 8h. Post-expansion antibody delivery, after epitope-preserving homogenization. (a, b) Widefield fluorescence images of Thy1-YFP-expressing mouse brain hemisphere slice before expansion (a), and after autoclave treatment and antibody staining (b). (c-h) Confocal micrographs of cortex from Thy1-YFP-expressing mouse brain treated with different disruption methods and antibodies, with anti-GFP (green, staining YFP) as a reference. (c) Autoclave method followed by staining against bassoon (blue) and homer (red). (d) Autoclaving followed by myelin basic protein staining. (e) Autoclaving followed by vimentin (red) and glial fibrillar acidic protein (blue) staining. (f) Staining for Lamin A/C after autoclave (i) or LysC (ii) treatment, or with secondary antibodies applied after LysC homogenization (with primaries previously anchored to the gel using AcX) (g-h) Comparison of staining before gelation (g) versus after disruption (h) using the autoclave method for Tom20 (i) and YFP (ii, shown in red channel in the bottom panel because the endogenous YFP is green), and after disruption using LysC for homer (red) and PSD-95 (blue) (iii). Scale bars: (a) 1 mm, (b) 1 mm (3.96 mm), (c-h) 5 µm (~21 µm).

FIG. 11a through FIG. 11f. Comparison of immunostaining methods with autoclave, LysC, and pre-gelation antibody treatment. Confocal images of Thy1-YFP expressing mouse cerebral cortex, immunostained pre-gelation followed by AcX treatment, gelation, and proteinase K digestion (proExM), column (i). Thy1-YFP brain samples immunostained after AcX treatment and gelation followed by autoclave treatment, column (ii), or by LysC digestion column (iii). Autoclave and LysC specimens all have YFP stained with anti-GFP (green) in addition to TOM20 (row (a)), homer (red) and bassoon (blue) (row (b)), homer (red) and post-synaptic density 95 (PSD95, blue) (row (c)), glutamic acid decarboxylase (GAD) 65/67 (row (d)), myelin basic protein (MBP, row (e)), and vimentin (red) and glial fibrillary acidic protein (GFAP, blue) (row (f)). Scale bars; 5 µm (~20 µm).

FIG. 15a through FIG. 15e. Pre- and post-expansion images of a Thy1-YFP mouse brain slice, and mouse brain with Brainbow 3.0 fluorescent proteins, and treated with proExM. (a) Pre-expansion wide-field image of Thy1-YFP brain slice. (b) Post-expansion wide-field image of the slice from a. (c) Post-expansion maximum intensity projection image (~10 µm in Z) of membrane bound GFP in Brainbow 3.0 mouse brain tissue. (d) One Z slice of the image from c. (e) Post-expansion imaging of two color imaging of membrane bound GFP and membrane bound mCherry in in Brainbow 3.0 mouse tissue. Scale bars: (a), (b) 500 µm (20.5 µm). (c-e) 5 µm (~20 µm).

DETAILED DESCRIPTION OF THE INVENTION

The terms "a", "an" and "the" as used herein are defined to mean "one or more" and include the plural unless the context is inappropriate.

International patent application serial number PCT/US15/16788, which is incorporated herein by reference and attached as Appendix A, teaches that the resolution of conventional microscopy can be increased by physically expanding specimens, a process termed 'expansion microscopy' (ExM). In ExM, chemically fixed and permeabilized tissue is infused with swellable material, undergoes polymerization, and the tissue-polymer composite is treated with protease to homogenize its mechanical characteristics. Next, dialysis in water resulted in a isotropically ~4-fold linear expansion, thereby achieving super-resolution with diffraction-limited microscopes, enabling rapid image acquisition and large field of view (Chen et al., Science, 347, 543 (2015)). The advantages to ExM include tissue clearing, resolution improvement, and higher tolerance to sectioning error due to the specimen expansion in the z-axis.

The invention provides a variant of ExM, named protein retention ExM (proExM), in which proteins, rather than labels, are anchored to the swellable gel, using a cross-linking molecule. Fluorescent signals from genetically encoded fluorescent proteins and conventional fluorescently labeled secondary antibodies and streptavidin that are directly anchored to the gel are preserved even when subjected to the nonspecific proteolytic digestion from the original ExM protocol. proExM is an extension of standard histological methods used to prepare samples for imaging.

Figure 7:
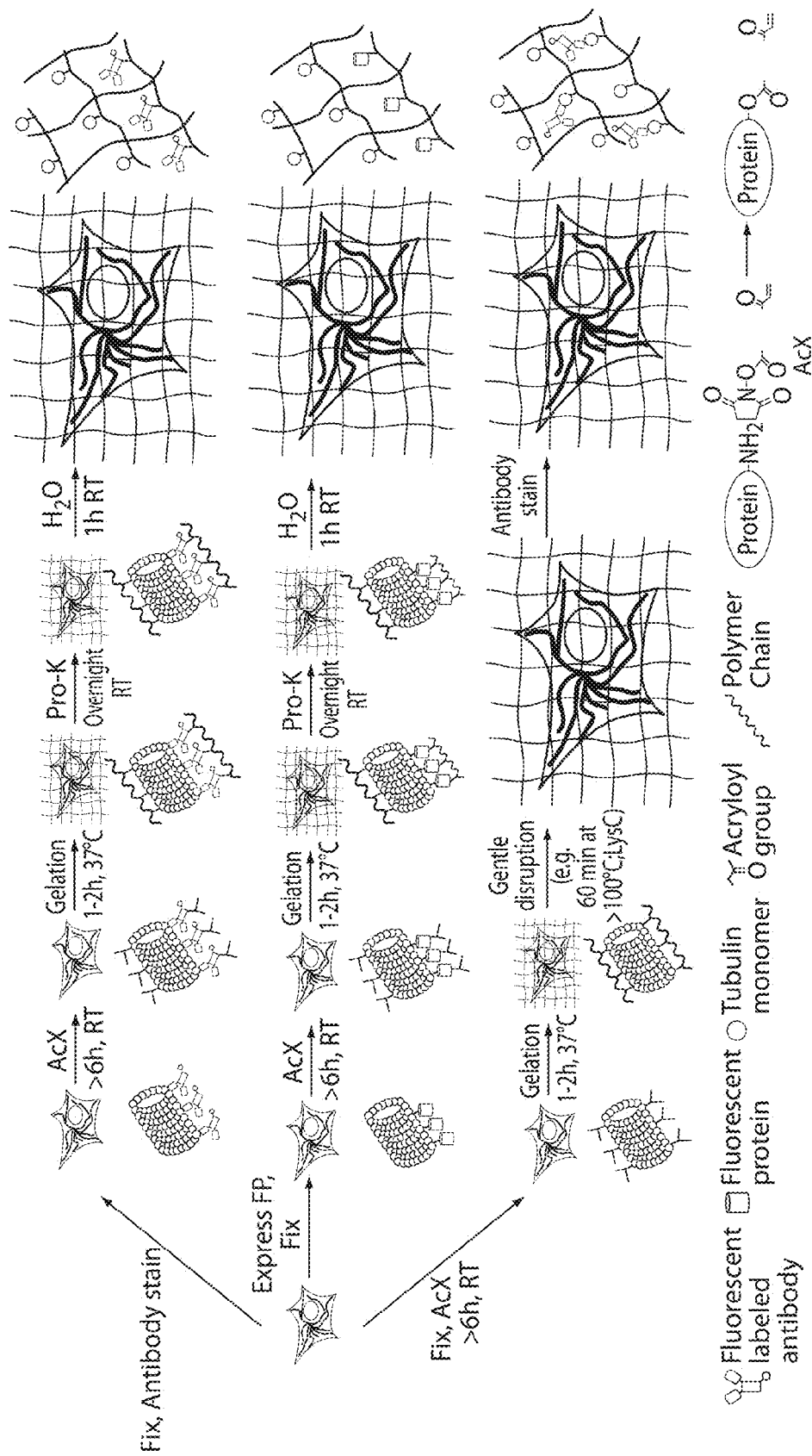
FIG. 7. Workflows for expansion microscopy with protein retention. Three basic sample processing workflows were explored in this paper. Top, samples are chemically fixed and stained with antibodies, using conventional immunostaining protocols, before AcX treatment at room temperature and subsequent ExM processing (gelation, proteinase K treatment, and expansion in water). Middle, samples expressing fluorescent proteins (FPs) are chemically fixed and (and optionally permeabilized) before AcX treatment, and subsequent ExM processing. Bottom, samples treated with AcX, followed by gelation, are then processed with a gentle homogenization procedure (e.g., alkaline hydrolysis and denaturation, or digestion with LysC), and finally antibody staining in the expanded state.
Figure 9A:
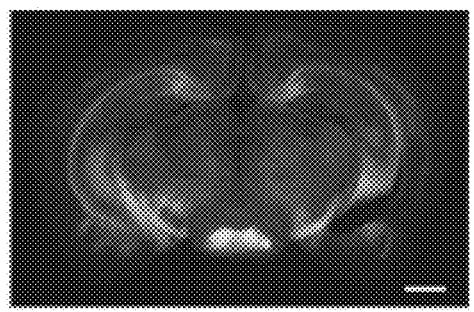
FIG. 9a through FIG. 9e. Pre- and post-expansion images of a Thy1-YFP mouse brain slice treated with AcX and LysC mild digestion method. (a) Pre-expansion wide-field image. (b) Post-expansion wide-field image. The arrow indicates the location of images (c-e). The bright edge surrounding the slice was the result of scattering at the gel-air interface. (c) Pre-expansion confocal image of a selected region of interest in hippocampus. (d) Post-expansion confocal image of the same selected region as (c). (e) Post-expansion DIC image of the same selected region as shown in (d). Scale bars: (a) 1 mm, (b) 4 mm (post-expansion units), (c) 5 µm,(d-e) 20 µm (post-expansion units).
Figure 9B:
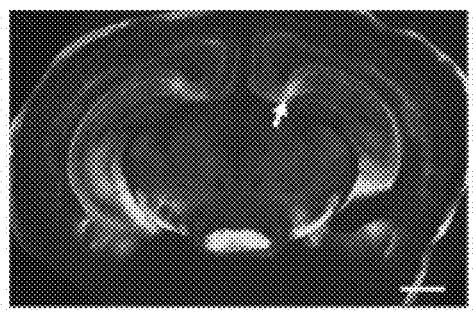
Figure 9C:
Figure 9D:
Figure 9E:
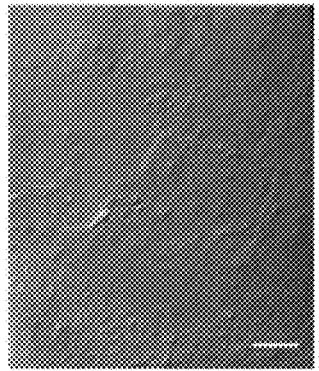
Figure 10A:
FIG. 10a and FIG. 10b. Incomplete homogenization with autoclave and LysC methods. Fluorescence images of Thy1-YFP expressing mouse cerebral cortex, with YFP stained with anti-GFP using confocal imaging after autoclave treatment and antibody staining, showing a discontinuous neurite not residing at the surface of the imaged volume (a), and using widefield imaging after LysC treatment and antibody staining, showing defects in the expansion regions containing white matter tracts (b). Scale bars; (a) 5 µm (~20 µm), (b) 0.5 mm (~2 mm).
Figure 10B:
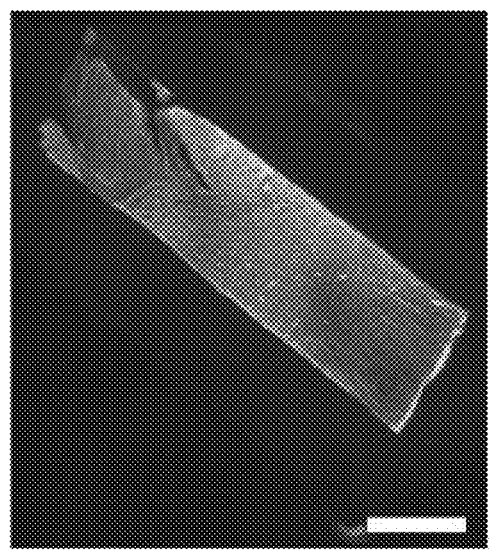
Figure 12A:
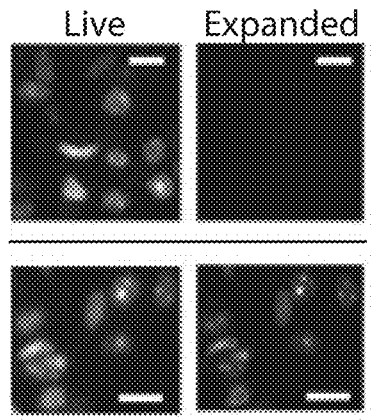
FIG. 12a through FIG. 12g. Control experiments of retention of EGFP and EYFP fluorescence in HEK293FT cells after proExM. (a) Representative images of EGFP-H2B fusion in live HEK293FT cells and following proExM treatment without (top) or with (bottom) the AcX treatment. Scale bar 20 (b) Percentage of EGFP fluorescence retained following proExM treatment without (left) or with (right) AcX treatment relative to live cells (mean±standard deviation, n=4). (c) Representative images of EGFP-H2B fusion in live HEK293FT cells (top left) and following proExM treatment in shrunk (top left) and fully expanded gel (bottom). Scale bar 5 µm. (d) Percentage of EGFP fluorescence retained following proExM treatment in shrunk (left) and fully (right) expanded gel relative to live cells (mean±standard deviation, n=4 samples). (e) Normalized curves of photobleaching of EGFP under wide-field illumination (475/34 nm, ~60 mW/mm$^2$ light power) measured in live (dashed line, n=8 cells) and proExM treated fully expanded HEK293FT cells (solid line, n=7 cells). (f) Normalized curves of photobleaching of EYFP under wide-field illumination (512/10 nm, ~8.4 mW/mm$^2$ light power) measured in live (dashed line, n=14 cells) and proExM treated fully expanded HEK293FT cells (solid line, n=5 cells). (g) Retention of EGFP and EYFP fluorescence in proExM treated HEK293FT cells upon long term storage in 1×PBS at 4° C. (n=3 samples).
Figure 12B:
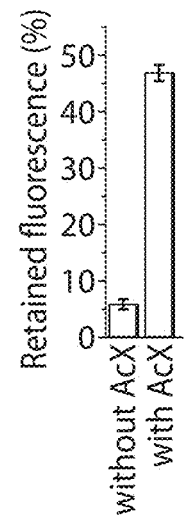
Figure 12C:
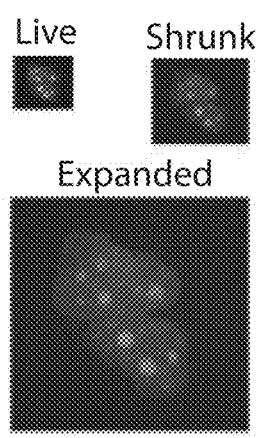
Figure 12D:
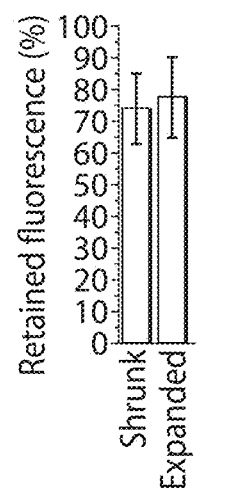
Figure 12E:
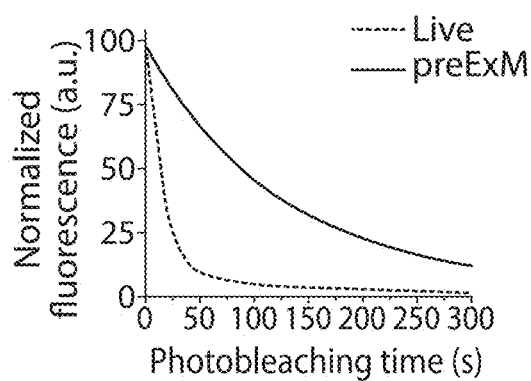
Figure 12F:
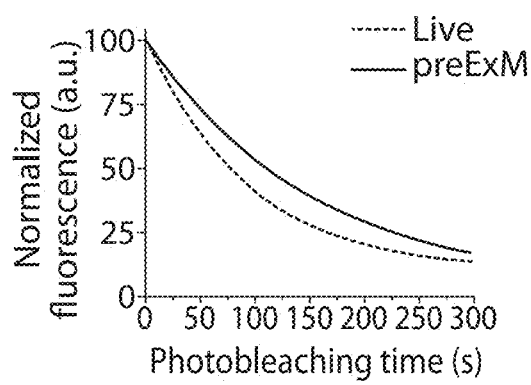
Figure 12G:
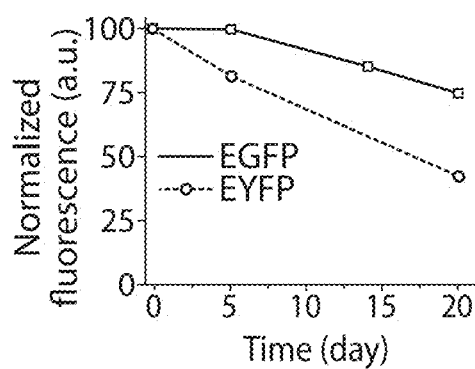

This protein retention ExM (proExM) strategy can be used to perform nanoscale imaging of immunostained cells and tissues (FIG. 7, top), as well as samples expressing various FPs (FIG. 7, middle). ProExM variants can support post-expansion antibody delivery, potentially increasing brightness of staining and antibody access (FIG. 7, bottom).

In one embodiment, the invention provides a method for the retention and imaging of proteins of a biological sample of interest comprising the steps of:

(a) conjugating proteins within the sample with a bifunctional crosslinker;
(b) embedding the sample in a swellable material wherein proteins within the sample are anchored to the swellable material;
(c) subjecting the sample to digestion;
(d) swelling the swellable material to form an expanded sample; and
(e) imagining the sample of interest.

In one embodiment, the bifunctional crosslinker comprises reactive groups to functional groups (e.g., primary amines or sulfhydryls) on proteins within the sample. The use of such a bifunctional crosslinker allows for proteins within the sample to be directly anchored to, or incorporate into, the swellable material. In one embodiment, the bifunctional crosslinker is a hetero-bifunctional crosslinker. Hetero-bifunctional crosslinkers possess different reactive groups at either end of a spacer arm, i.e., atoms, spacers or linkers separating the reactive groups. These reagents not only allow for single-step conjugation of molecules that have the respective target functional group, but they also allow for sequential (two-steps) conjugations that minimize undesirable polymerization or self-conjugation.

In one embodiment, the bifunctional crosslinker comprises a protein-reactive chemical moiety and a gel-reactive chemical moiety (i.e., a swellable material-reactive chemical moiety). The protein-reactive chemical group includes, but is not limited to, N-hydroxysuccinimide (NHS) ester, thiol, amine, maleimide, imidoester, pyridyldithiol, hydrazide, phthalimide, diazirine, aryl azide, isocyanate, or carboxylic acid, which, for example, can be reacted with amino or carboxylic acid groups on proteins or peptides. In one embodiment, the protein-reactive groups include, but are not limited to, N-succinimidyl ester, pentafluorophenyl ester, carboxylic acid, or thiol. The gel-reactive groups include, but are not limited to, vinyl or vinyl monomers such as styrene and its derivatives (e.g., divinyl benzene), acrylamide and its derivatives, butadiene, acrylonitrile, vinyl acetate, or acrylates and acrylic acid derivatives.

In one embodiment, the chemical to anchor proteins directly to any swellable material is a succinimidyl ester of 6-((acryloyl)amino)hexanoic acid (acryloyl-X, SE; abbreviated "AcX", Life Technologies). Treatment with AcX modifies amines on proteins with an acrylamide functional group. The acrylamide functional groups allows for proteins to be anchored to the swellable material as it is synthesized in situ.

In one embodiment, the proteins of the sample of interest can be modified with the protein-reactive group and the gel-reactive group in separate steps using click chemistry. Click chemistry, also referred to as tagging, is a class of biocompatible reactions intended primarily to join substrates of choice with specific biomolecules. In this method, proteins of the sample of interest are treated with a protein-reactive group comprising a click group and then treated with a gel-reactive group comprising a complementary click group. Complementary groups include, but are not limited to, azide groups and terminal alkynes (see e.g., H. C. Kolb; M. G. Finn; K. B. Sharpless (2001). *"Click Chemistry: Diverse Chemical Function from a Few Good Reactions"*. Angewandte Chemie International Edition. 40(11): 2004-2021, which is incorporated herein by reference).

In some embodiments, native proteins anchored to the swellable material perfused throughout the sample as described herein can retain epitope functionality and be labeled post-expansion if the nonspecific proteolysis of ExM is replaced with modified post-gelation homogenization treatments. Such approaches may overcome the limitations inherent to delivering antibodies in the crowded environment of native tissue[15-19]. For example, closely packed epitopes may bind antibodies poorly in dense tissue, but better access antibodies after expansion (FIG. 8).

In one embodiment, the digestion comprises treating gel-embedded tissues, e.g., Thy1-YFP mouse brain samples, in an alkaline detergent-rich buffer for one hour in an autoclave (FIG. 8a, showing endogenous YFP pre-treatment; FIG. 8b, showing post-expansion labeling with anti-GFP). In another embodiment, the digestion comprises exposing gel-embedded tissues to LysC, which cuts proteins at Lys residues (in contrast to nonspecific proteinase K)[4,5] (FIG. 9). It was found that antibodies could indeed be delivered successfully post-expansion (FIG. 8c-e).

Figure 4A:
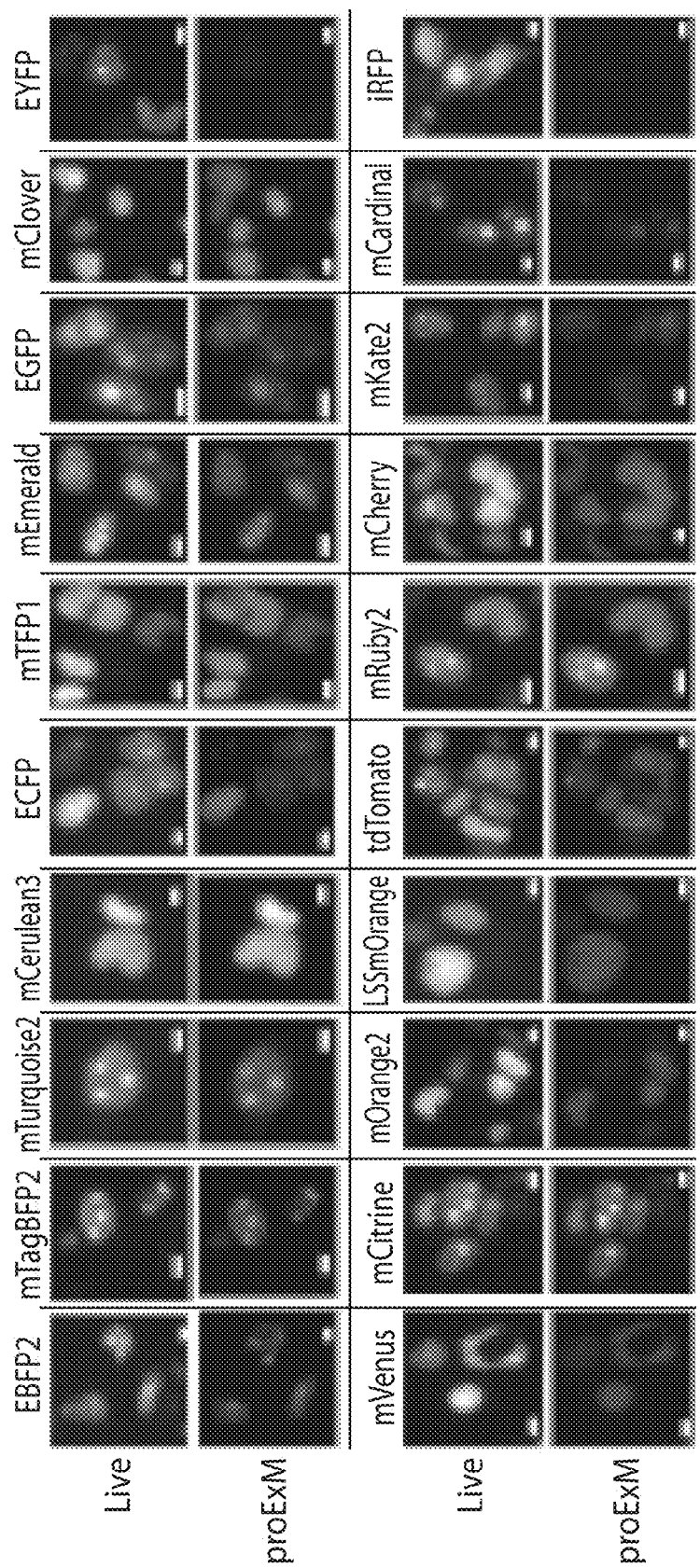
FIG. 4a through FIG. 4l. Retention of fluorescent protein (FP) and antibody fluorescence signals in proExM and proExM of FP fusions. (a) Representative images of selected FP-histone fusion proteins in live HEK293FT cells (upper row) and in the same cells after proExM treatment (lower row); iRFP was expressed as N-terminal fusion with nuclear localization sequence (NLS). (b) Quantified fluorescence of experiments as in panel a, after proExM treatment (cross-hatched bars; mean±standard deviation; n=4 transfection replicates each). Open bars, literature values of the brightnesses of these fluorophores, normalized to the brightness of EGFP. (c) Retention of fluorescence for selected dyes conjugated with antibodies, after proExM treatment (mean±standard deviation, n=3 samples each), in mouse brain slice. (d) Super-resolution structured illumination microscopy (SR-SIM) image of immunostained microtubules after the anchoring step vs. (e) post-expansion image of the same sample acquired with a spinning disk confocal microscope. (f) Root mean square (RMS) length measurement error as a function of measurement length for proExM vs SIM images (blue line, mean; shaded area, standard deviation; n=4 samples). (g) Confocal image of mClover-α-tubulin fusion. HeLa cells are used throughout the rest of this figure. Panels (i and ii) are magnified views of boxed regions in (g). Linecuts are quantified in panels h, i. Solid red lines in (h, i) indicate the Gaussian fit used to determine the full width at half maximum (FWHM; illustrated with red arrows). (j) Confocal image of mEmerald-clathrin fusion (left) and magnified views of single CCPs in the boxed regions (right). (k) Dual color proExM of clathrin (fused to mEmerald, green) and keratin (mRuby2, red). (l) Dual color proExM image of actin (mRuby2, red) and paxillin (mEmerald, green) fusions. Panels (i and ii) are magnified views of boxed regions in (f). Scale bars: (a) 5 µm,(d) 5 µm(e) 5 µm (physical size post-expansion, 20.5 µm(g) 5 µm (21.5 µm), (i-ii) 1 µm; (j) 10 µm (42.6 µm), insets 200 nm; (k) 1 µm (4.3 µm), (l) 5 µm (21.5 µm), (i-ii) 1 µm.

In a further embodiment, the invention provides a method that combines the convenience of direct protein anchoring with strong enzymatic, for example proteinase K, digestion. Treatment with AcX followed by the standard ExM workflow, including proteinase K digestion, can preserve fluorescence in the expanded gel with high efficiency (65±5% preservation; mean±std. dev.; n=4; FIG. 4a, 5b and FIG. 12).

The persistence of fluorescence for various fluorescent proteins ("FPs") in the proExM workflow was systematically examined. 20 widely used FPs with spectra ranging from the blue to the near-infrared were selected (Table 1).

TABLE 1

Performance of selected FPs in proExM.

| Protein | Ex max, nm | Em max, nm | Molecular brightness relative to EGFP, % | Brightness in proExM cells, % of live cells | Addgene plasmid code | Reference |
|---|---|---|---|---|---|---|
| EBFP2 | 383 | 448 | 54 | 62 ± 4 | 55243 | 29 |
| mTagBFP2 | 399 | 454 | 98 | 65 ± 9 | 55302 | 30 |
| mTurquoise2 | 434 | 474 | 85 | 68 ± 8 | 36207 | 31 |
| mCerulean3 | 433 | 475 | 105 | 69 ± 4 | 55421 | 32 |
| ECFP | 434 | 477 | 39 | 51 ± 2 | 55344 | 33, 34 |
| mTFP1 | 462 | 492 | 165 | 70 ± 7 | 55488 | 35 |
| mEmerald | 487 | 509 | 118 | 53 ± 4 | 54112 | 36 |
| EGFP | 489 | 509 | 100 | 65 ± 5 | 56436 | 37 |
| mClover | 505 | 515 | 128 | 61 ± 4 | 56533 | 38 |
| EYFP | 514 | 527 | 155 | 64 ± 7[c] | 56592 | 39 |
| mVenus | 515 | 528 | 159 | 44 ± 5 | 56615 | 40 |
| mCitrine | 516 | 529 | 177 | 54 ± 7 | 56555 | 41 |
| mOrange2 | 549 | 565 | 105 | 32 ± 2 | 57962 | 42 |
| LSSmOrange | 437 | 572 | 71 | 42 ± 3 | 37133 | 43 |
| tdTomato | 554 | 581 | 144 | 67 ± 4 | 58102 | 44 |
| mRuby2 | 559 | 600 | 130 | 90 ± 7 | 55898 | 38 |
| mCherry | 587 | 610 | 48 | 72 ± 3 | 55056 | 44 |
| mKate2 | 588 | 633 | 76 | 37 ± 3 | NA[a] | 45 |
| mCardinal | 604 | 659 | 50 | 36 ± 3 | 56161 | 46 |
| iRFP | 690 | 713 | 15 | 14 ± 1 | NA[b] | 47 |

[a]mKate2 gene from Addgene plasmid 37132 was swapped with LSSmOrange gene in Addgene plasmid 37133.
[b]cloned as N-terminus fusion with nuclear localization sequence.
[c]since EYFP is particularly sensitive to the high Cl⁻ used to shrink the gel[48], retention of EYFP fluorescence was measured in fully expanded gel.

Figure 4B:
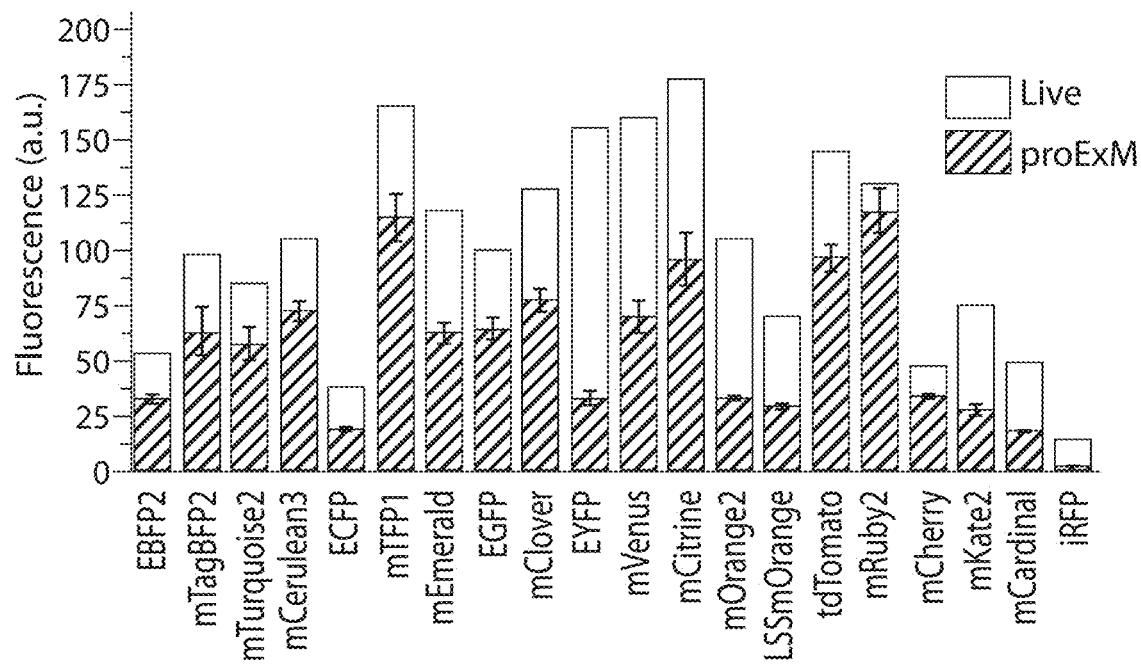

Selected FPs were fused to histone proteins and expressed in human embryonic kidney (HEK293FT) cells. Images of live cultures vs. after-proExM images of the same cells were compared (FIG. 4a). Most FPs retained more than 50% of their live fluorescence intensity after proExM (n=4 samples each; FIG. 4a, 4b, Table 1), comparable to the persistence of small-molecule fluorophores in the original ExM protocol[1].

Figure 4C:
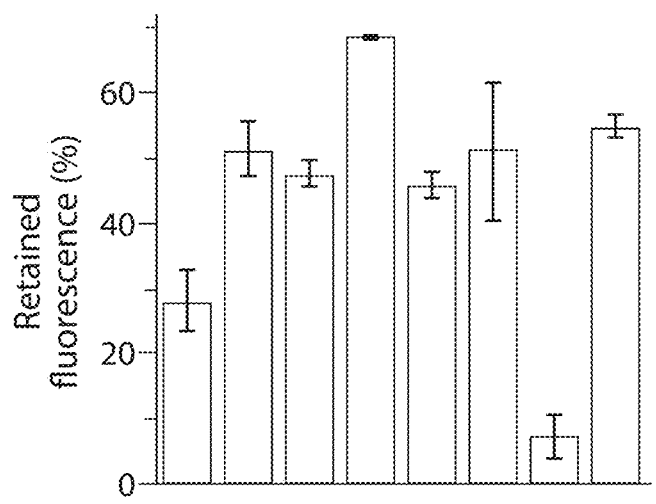

Having seen that FPs could persist sufficiently to report signals even after a strong digestion process, it was determined that proExM anchors and preserves the fluorescence of fluorescently conjugated secondary antibodies. Following gelation and digestion, specimens labeled with secondary antibodies bearing a variety of small-molecule fluorophores retained ~50% of their initial brightness (n=3 samples each; FIG. 4c; Table 2).

TABLE 2

Performance of selected secondary antibody dyes in proExM.

| Dye | Ex max, nm | Em max, nm | Brightness in proExM as % of post antibody stain | Source |
|---|---|---|---|---|
| DyLight405 | 400 | 421 | 28 ± 5 | Life Technologies |
| CF405M | 408 | 452 | 51 ± 4 | Biotium |
| Alexa488 | 495 | 519 | 48 ± 2 | Life Technologies |
| Alexa546 | 556 | 573 | 68 ± 3 | Life Technologies |
| Alexa594 | 590 | 617 | 46 ± 2 | Life Technologies |
| CF633 | 630 | 650 | 51 ± 10 | Biotium |
| Alexa647 | 650 | 668 | 7 ± 3 | Life Technologies |
| Atto647N | 644 | 669 | 55 ± 2 | Sigma |

Therefore, proExM allows for the use of commercial secondary antibodies rather than required the need for custom formulations.

Figures 13A, 13B, 13C:
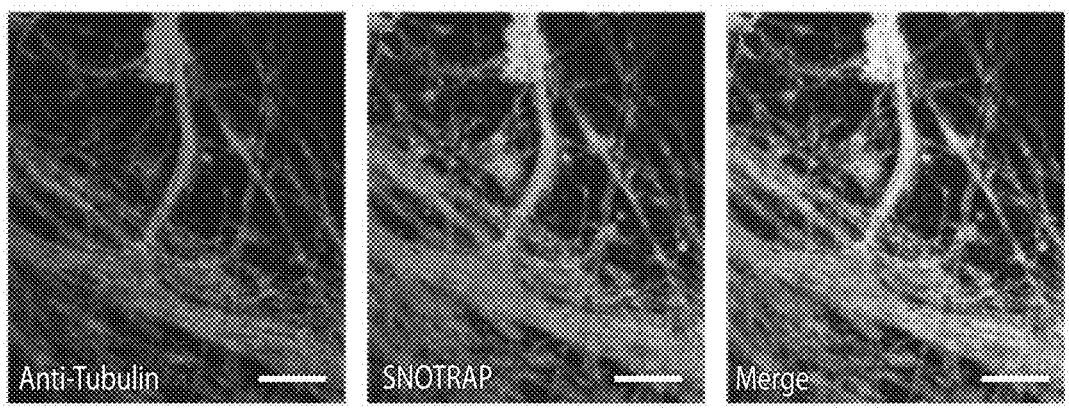
FIG. 13a through FIG. 13c. ProExM imaging of S-nitrosylation. (a) ProExM of tubulin fibers stained with Anti-Tubulin in primary neuron culture. (b) ProExM of fluorescently labeled streptavidin bound to biotinylated cysteine S-nitrosylated proteins chemically tagged via the SNO-TRAP method. (c) Color composite of (a) and (b) (tubulin, red; SNOTRAP, green).
Figure 14A:
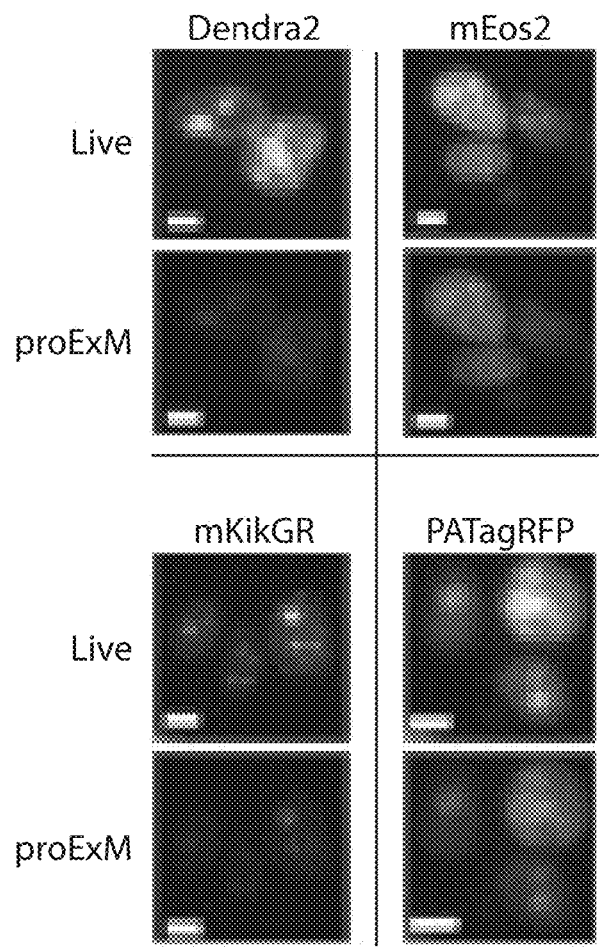
FIG. 14a through FIG. 14g. Performance of selected photoswitchable and photoactivatable FPs in proExM. (a) Representative images of selected photoswitchable/photoactivatable FP-histone fusions in live HEK293FT cells (live, upper image for each FP) and in the same cells after proExM treatment (proExM, lower image for each FP). (b) Fluorescence of selected FP-histone fusions in HEK293FT cells before (live, open bars) and after proExM treatment (proExM, crosshatched bars, mean±standard deviation, n=4 transfection replicates each). Fluorescence of selected FPs normalized to their molecular brightness relative to EGFP. (c) Averaged intensity image of 100 consecutive frames of unconverted H3.3-Dendra2 within a nucleus of a HEK293 cell after proExM, excited by a 488 nm laser. (d) PALM image derived from 10,000 consecutive frames of cell in c, which was photoconverted using low-power continuous 405 nm laser excitation. The 196,441 detected particles are displayed using Gaussian mask estimation according to their localization full-width at half-maximum. The mean and median localization errors for the H3.3-Dendra2 fusion were 23.3 nm. (e) Distribution of the total number of photons from mEos2-α-tubulin (mean 196.6, median 169.6). (f) The mean and median localization errors for the mEos2-α-tubulin fusion were 26.1 and 25.9 nm, respectively. (g) PALM image derived from 15,000 consecutive frames of proExM treated HeLa cell expressing mEos2-α-tubulin, which was photoconverted using low-power continuous 405 nm laser excitation. The 3.15 million detected particles are displayed using Gaussian mask estimation according to their localization full-width at half-maximum. Scale bars: (a) 10 µm,(c-d, g) 2.2 µm (physical size post-expansion, 10 µm).
Figure 14B:
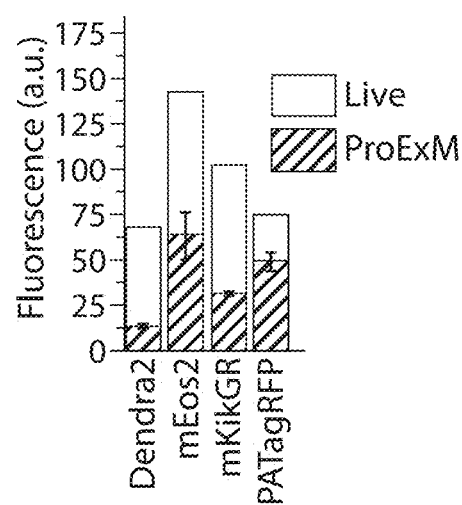
Figure 14C:
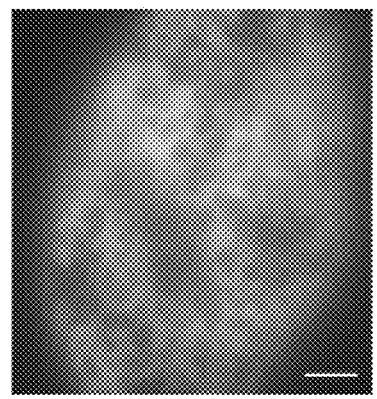
Figure 14D:
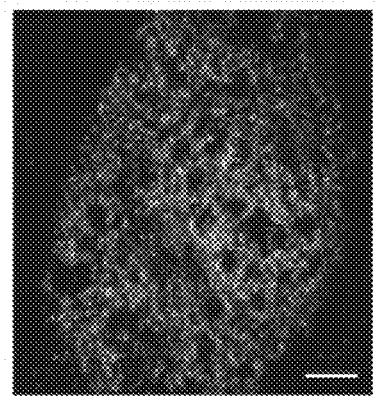
Figure 14E:
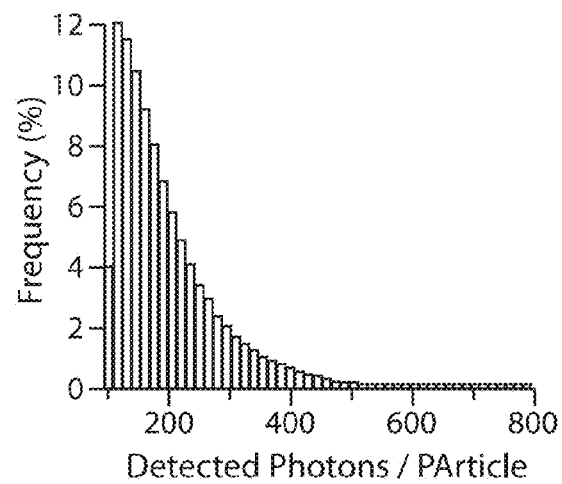
Figure 14F:
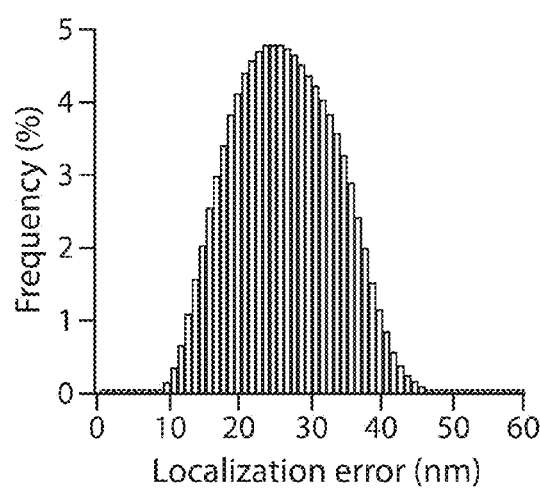
Figure 14G:
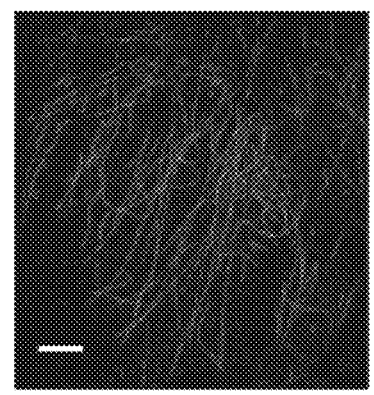
Figure 16A:
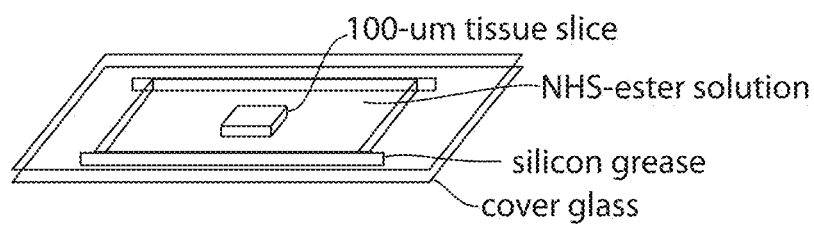
FIG. 16a through FIG. 16g. Optimizing AcX penetration depth in fixed brain tissue. (a) Chamber assay for measuring penetration depth of a NHS-ester mixture (99% AcX+1% NHS-biotin, which has similar molecular weight and charge as AcX) from the side of a tissue slice. After overnight treatment with the NHS-ester mixture, slices were retrieved, washed and treated with fluorophore-conjugated streptavidin to visualize penetration of NHS-ester mixture. (b) Representative image of a 100-µm-thick mouse brain slice stained under the chamber assay conditions. Scale bar 1 mm. (c) Fluorescent intensity along the line-cut represented as the white dashed line in b. The distance over which the intensity drops from maximum to half of its value ($D_{1/2}$) is a characteristic length for the depth of NHS-ester penetration. (d, e) Staining with IVIES-based saline (MBS; 100 mM MES+ 150 mM NaCl) yields significantly improved depth of NHS-ester penetration than phosphate-based saline (PBS) over all pH levels tested. Scale bar 1 mm. (f, g) Staining at 4° C. yields moderately greater depth of penetration than at RT. Scale bar 1 mm.
Figure 16B:
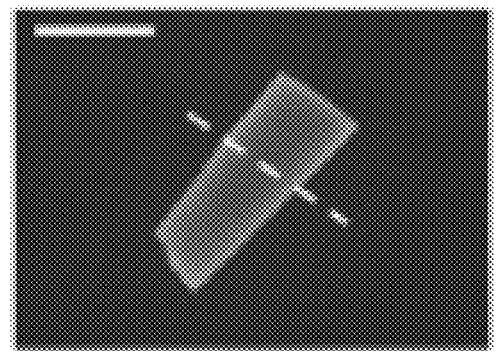
Figure 16C:
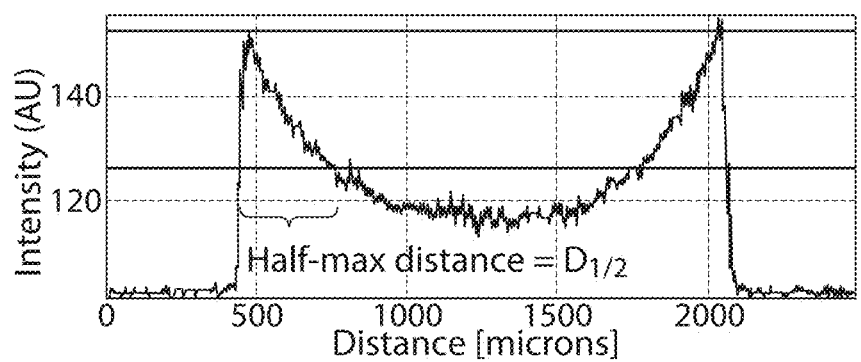
Figure 16D:
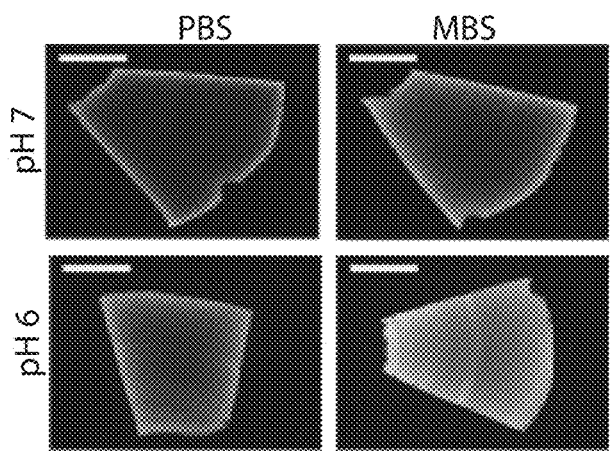
Figure 16E:
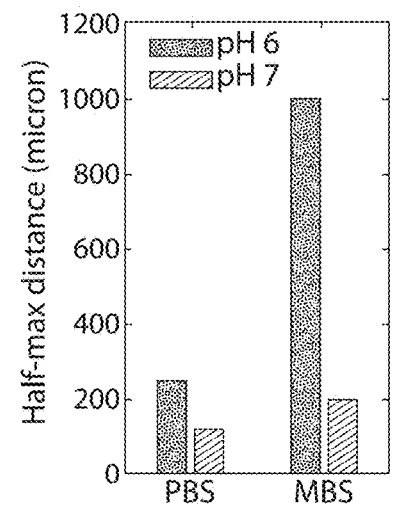
Figure 16F:
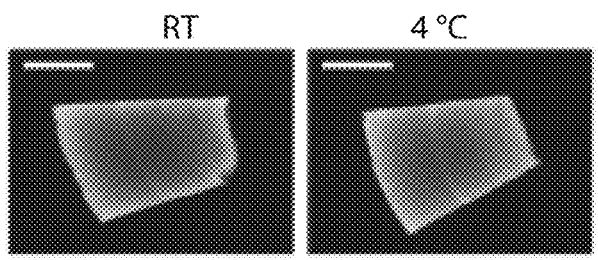
Figure 16G:
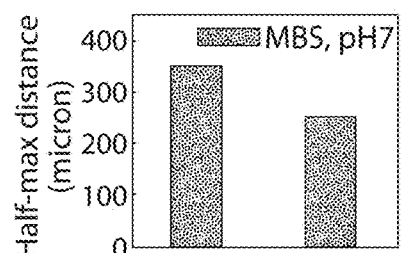

In addition to antibodies, the preservation of signals from fluorescently labeled streptavidin was observed. Using streptavidin, probes designed to capture cysteine-S-nitrosation using a previously developed chemical method, SNO-TRAP[8], were imaged thus demonstrating the imaging of S-nitrosation signals with proExM (FIG. 13). This protocol also points towards the possibility of anchoring other protease-resistant tags to the polymer, followed by gelation, digestion, expansion, and imaging, as a potentially generalized strategy.

Figure 4D:
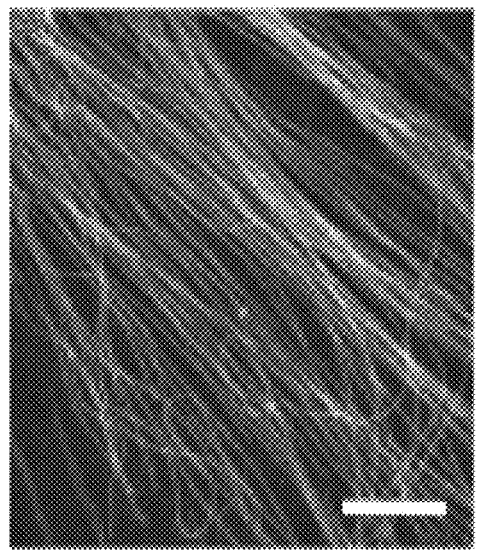
Figure 4E:
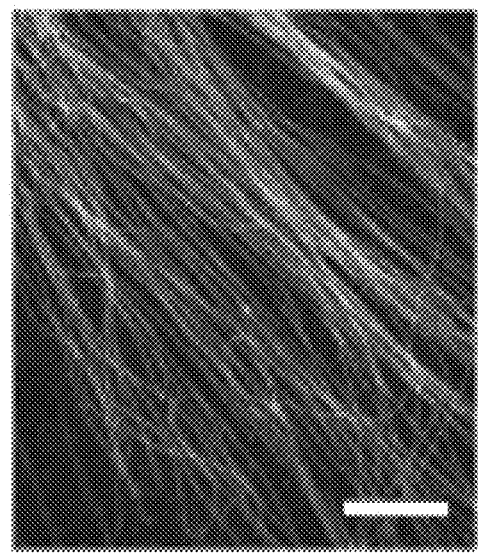
Figure 4F:
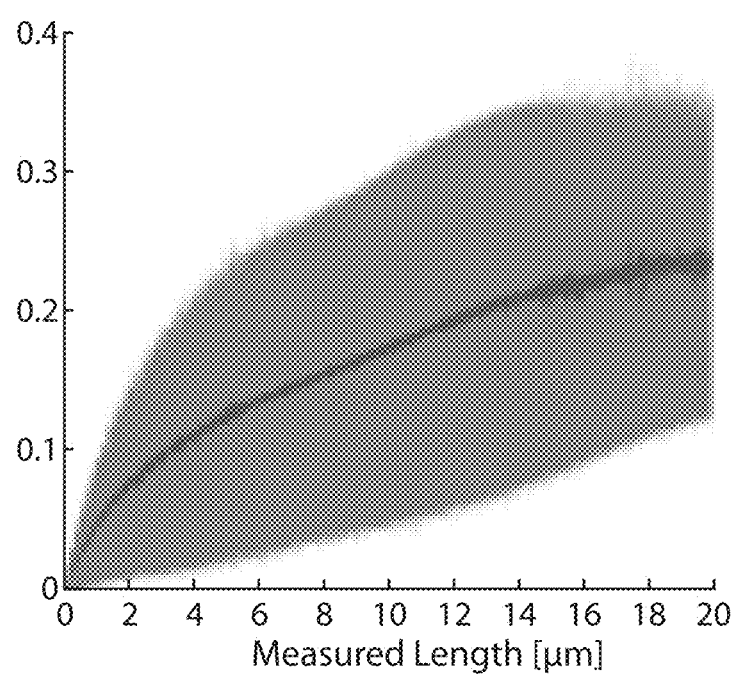
Figure 4G:
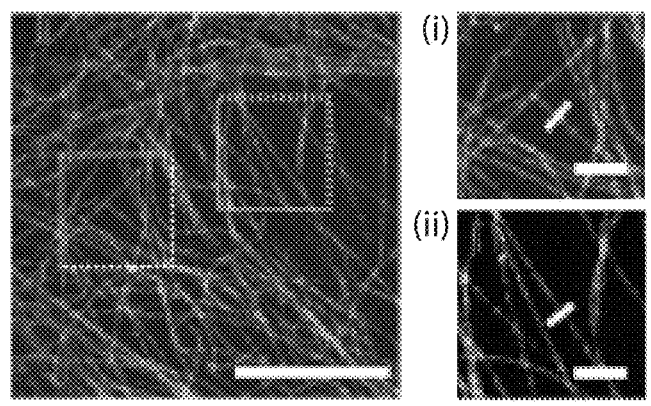
Figure 4H:
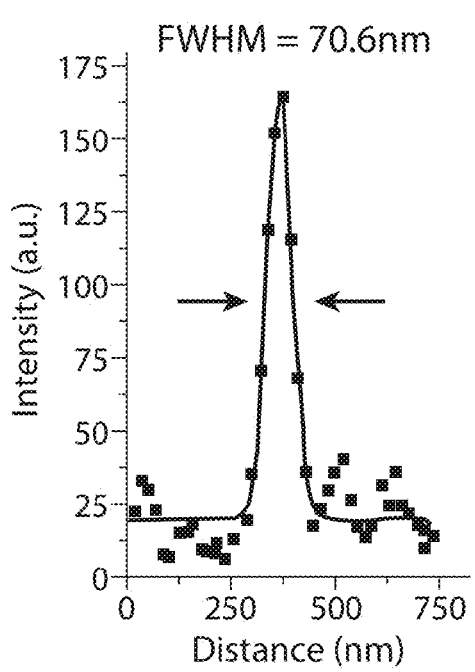
Figure 4I:
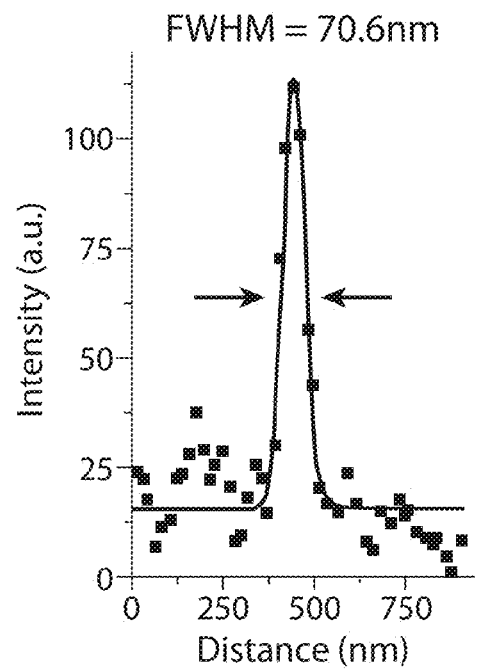
Figure 4J:
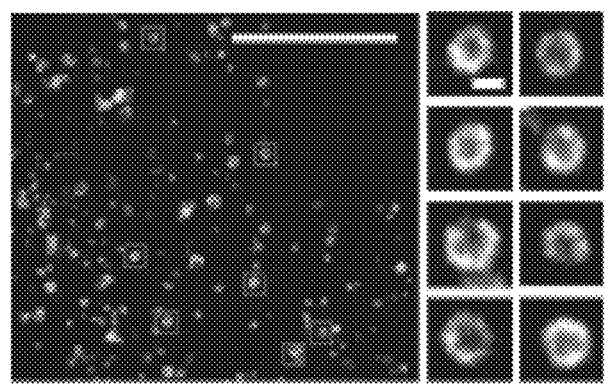
Figure 4K:
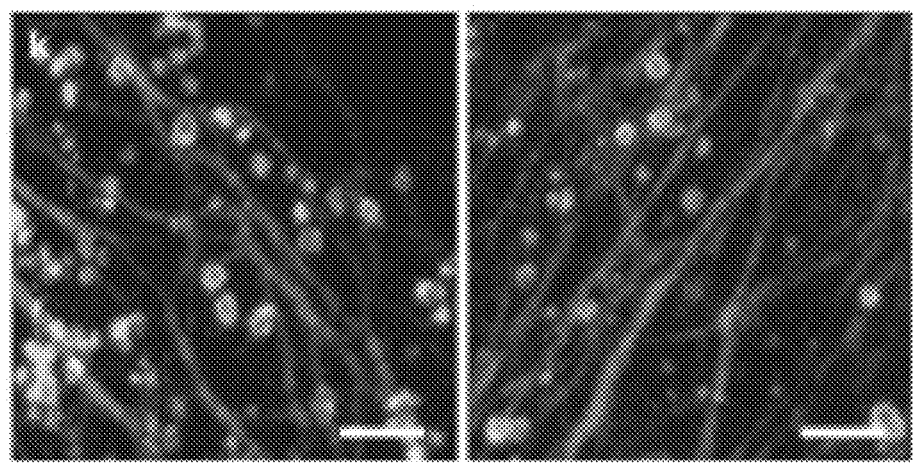
Figure 4L:
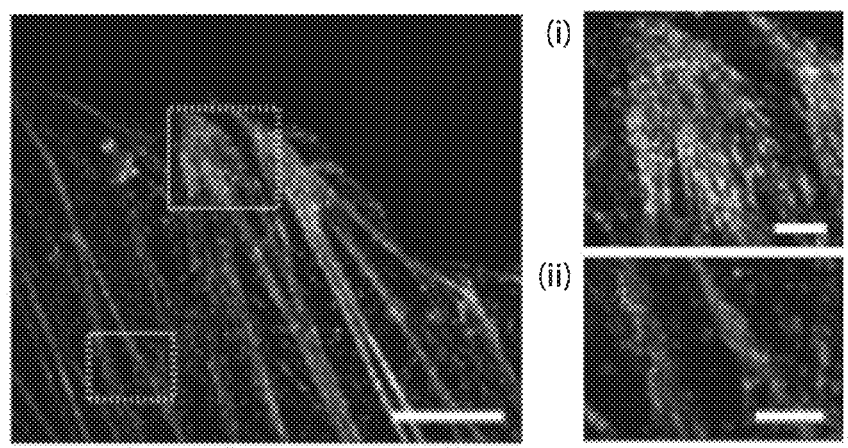

Although the digestion step preserved the nanoscale isotropy of the expanded specimen, validation of proExM by performing imaging of immunostained microtubules in cultured cells with super-resolution structured illumination microscopy (SR-SIM) (FIG. 4d) before proExM and confocal imaging after proExM (FIG. 4e). The root-mean-square (RMS) error of feature measurements after proExM over length scales between 0 and 20 microns was quantified, and found that RMS errors were ~1-2% of the measurement distance (FIG. 4f).

proExM followed by confocal microscopy was performed to image several fusion proteins bearing genetically encoded fluorophores (i.e., unstained) in cultured HeLa cells. Fusions of tubulin, clathrin and keratin were examined (FIG. 4g-k), which are commonly used as stereotyped structures to demonstrate super-resolution imaging of cells[9-12]. The tubulin-mClover fusion presented a microtubule full-width at half-maximum (FWHM) of 67±8 nm (n=16 microtubules in 3 samples) (FIG. 4h, i), suggesting a resolution of better than 70 nm[11]. Clathrin-mEmerald in HeLa cells were also imaged obtaining excellent definition of the nulls in the middle of the pits (FIG. 4j). Dual-color proExM imaging of fusion proteins containing mEmerald and mRuby2, two of the genetically encoded fluorophores in the screen, yielded excellent image quality as expected (keratin-mRuby2 and clathrin-mEmerald, FIG. 4k; paxillin-mEmerald and actin-mRuby2, FIG. 4l). The stability of four photoswitchable FPs were examined during proExM (FIG. 14, Table 3).

TABLE 3

Performance of selected photoswitchable and photoactivatable FPs in proExM.

| Protein | Ex max, nm | Em max, nm | Molecular brightness relative to EGFP, % | Brightness in proExM cells, % of live cells | Addgene plasmid code | Reference |
|---|---|---|---|---|---|---|
| Dendra2 | 490 | 507 | 68 | 21 ± 3 | 57725 | 49 |
|  | 553 | 573 | 58 | ND |  |  |
| mEos2 | 506 | 519 | 143 | 45 ± 9 | 57384 | 50 |
|  | 573 | 584 | 92 | ND |  |  |
| mKikGR | 505 | 515 | 102 | 31 ± 2 | 57326 | 51 |
|  | 580 | 591 | 53 | ND |  |  |
| PATagRFP | 562 | 595 | 76 | 66 ± 7 | NA[a] | 52 |

Cells expressing histone 2B-Dendra and mEos2-tubulin fusions were imaged with PALM microscopy (FIG. 14), demonstrating preservation of photoswitching fluorophores compatible with PALM.

Figure 5E:
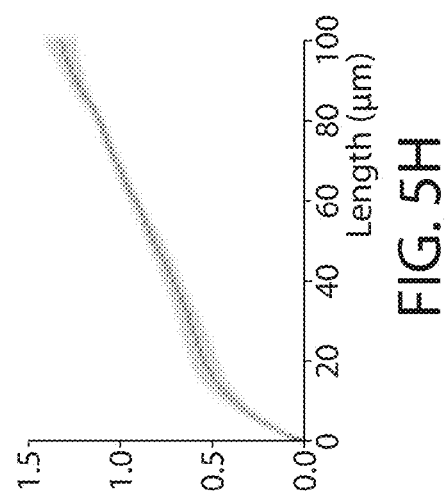
FIG. 5a through FIG. 5p. Validation of proExM in different mammalian tissue types. (a-d) Low magnification, wide-field images of pre-expansion (top) and post-expansion (bottom) samples of Thy1-YFP mouse brain (a) and vimentin-immunostained mouse pancreas (b), spleen (c), and lung (d). (e) Composite fluorescence image of Tom20 in Thy1-YFP mouse brain imaged with super-resolution structured illumination microscopy (SR-SIM) (green) and proExM (purple) with conventional confocal microscopy with distortion vector field overlaid (white arrows). (f) Pre-expansion SR-SIM image showing boxed region in (a). (g) Post-expansion confocal image of (f). (h) RMS length measurement error as a function of measurement length for proExM vs SR-SIM pre-expansion for Tom20 staining in Thy1-YFP mouse brain (blue line, mean; shaded area, standard deviation; n=3 mouse brain cortex samples). (i) High magnification, wide-field fluorescence composite image of vimentin in mouse pancreas before (green) and after (purple) expansion with distortion vector field overlaid (white arrows, see methods). (j) Pre-expansion wide-field image showing boxed region in (i). (k) Post-expansion image of (j). (l) Root mean square (RMS) length measurement error as a function of measurement length for proExM vs widefield pre-expansion images for the different tissue types in (b-d) (blue line, mean; shaded area, standard deviation; n=3 samples from pancreas, spleen, and lung). (m) Composite fluorescence image of vimentin in mouse pancreas imaged with super-resolution structured illumination microscopy (SR-SIM) (green) and proExM (purple) with conventional confocal microscopy with distortion vector field overlaid (white arrows). (n) Pre-expansion SR-SIM image showing boxed region in (m). (o) Post-expansion confocal image of (n). (p) RMS length measurement error as a function of measurement length for proExM vs SR-SIM pre-expansion for vimentin staining in pancreas (blue line, mean; shaded area, standard deviation; n=4 fields of view from 2 samples). Scale bars: (a) top 200 µm, bottom 200 µm (physical size post-expansion, 800 µm), (b-d) top 500 µm, bottom 500 µm (2.21 mm, 2.06 mm, 2.04 mm, respectively), (e, f) 10 µm, (g) 10 µm (40 µm), (i) 10 µm, (j) 5 µm, (k) 5 µm (20.4 µm), (m) 5 µm, (n) 5 µm, (o) 5 µm (20.65 µm).
Figure 5F:
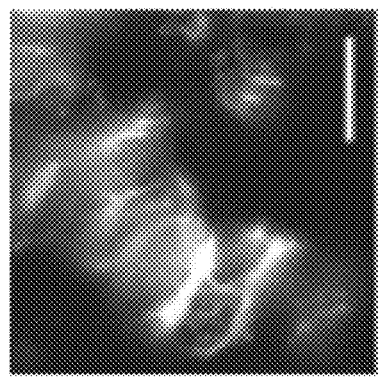
Figure 5G:
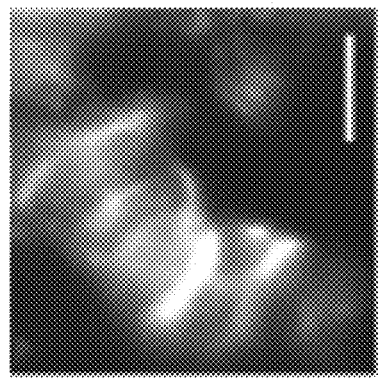
Figure 5H:
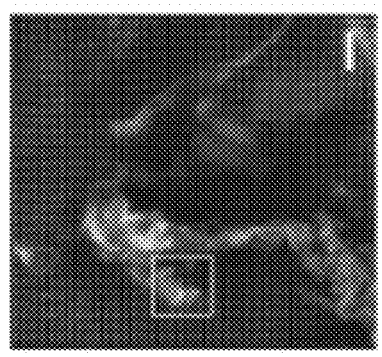

To assess the performance of proExM in various three-dimensional tissues, proExM was performed on four different mouse tissue types (brain, pancreas, lung and spleen, FIG. 5a-d). Mouse brain expressing YFP under the Thy1 promoter (Thy1-YFP) in a sparse subset of neurons expands without distortion at the millimeter scale following treatment with proteinase K as described for cultured cells (FIG. 5a, top vs. bottom). Pancreas, spleen and lung have different mechanical properties than brain (e.g., more connective tissue), which hinders expansion following room temperature proteinase K digestion. The intermediate filament vimentin was antibody stained as a marker of connective tissue to examine the isotropy of expansion in these diverse tissue types. proExM allowed for expansion of pancreas, lung, and spleen tissue, with excellent preservation of tissue morphology at the millimeter length scale (FIG. 5b-d, top vs. bottom). High-resolution diffraction-limited microscopy of the tissue before (FIG. 5e, 5f) vs after proExM (FIG. 5e, 5g) shows the resolution improvement of proExM. The isotropy of expansion was quantified by measuring the root-mean-square (RMS) error of feature measurements after proExM in the microscale (<100 μm) for pancreas, lung and spleen tissue. The RMS errors were small (1-3% of the measurement distance) and similar among all three of the tissue types (FIG. 5h) at this length scale.

Figure 5L:
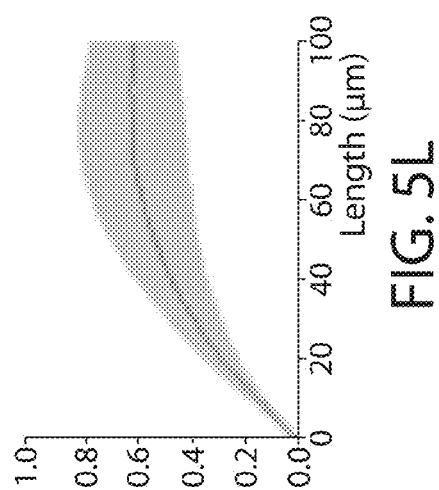
Figure 5K:
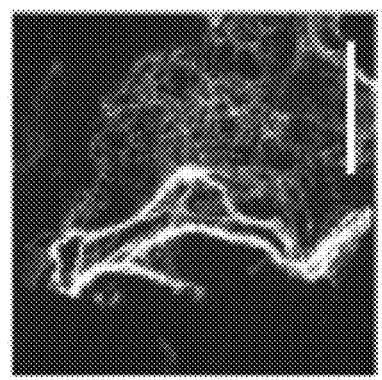
Figure 5J:
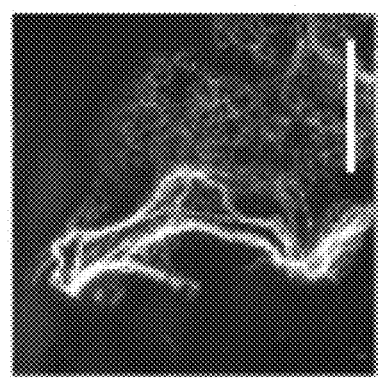
Figure 5I:
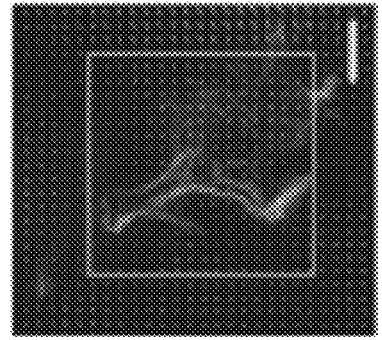
Figure 5P:
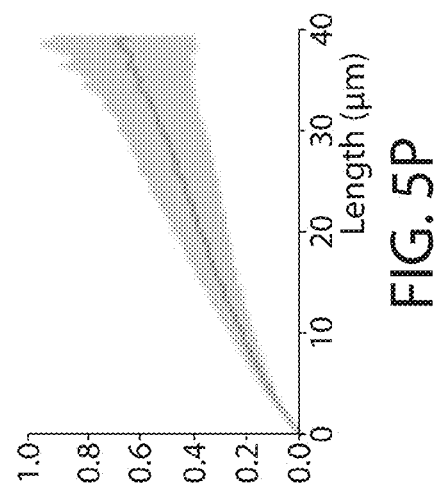
Figure 5O:
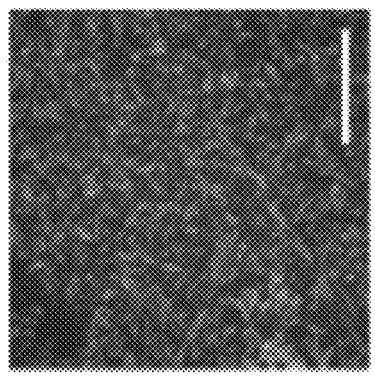
Figure 5N:
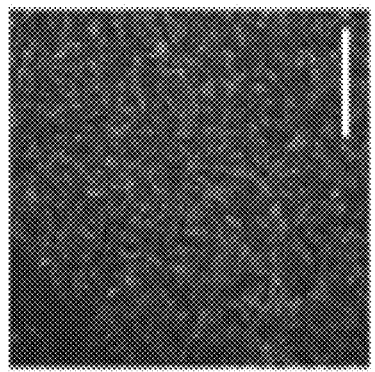
Figure 5M:
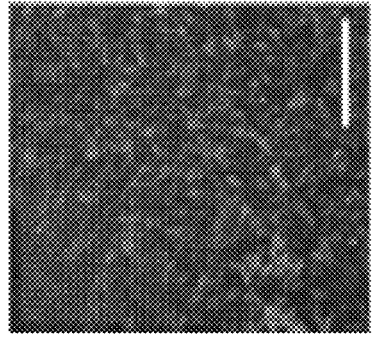

To examine the isotropy of expansion at the nanoscale, SR-SIM (FIG. 5i, 5j) and proExM confocal imaging (FIG. 5i, 5k) were performed on vimentin staining in the pancreas. Again, small RMS errors on the order of 1-5% of the measurement length for measurements between 0 and 25 microns were observed (FIG. 5l, n=4 fields of view from 2 samples). A similar analysis was performed on mouse brain cortical tissue stained with antibodies against Tom20, a mitochondrial marker, and imaged with SR-SIM before (FIG. 5m, 5n) and confocal after (5o) proExM processing using proteinase K digestion at room temperature. RMS errors for this tissue type were between 1-3% of the measurement length, between 0 and 40 microns (FIG. 5p, n=3 specimens).

Figure 6A:
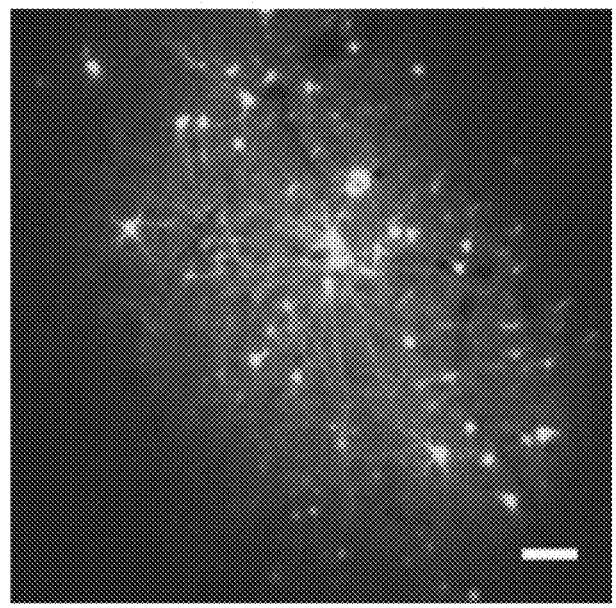
FIG. 6a through FIG. 6h. proExM of mammalian brain circuitry. (a) Wide-field image of GFP fluorescence in virally injected rhesus macaque cortex. (b) Post-expansion wide-field fluorescence image of (a). (c) Volume rendering of confocal microscopy images of subregion of (b). Inset shows a zoom-in of boxed region in (c) showing dendritic spines. (d) Low magnification widefield fluorescence imaging showing immunostained mouse hippocampus expressing virally delivered Brainbow3.0. (e) Post-expansion wide-field image of sample from (e). (f) MIP high resolution confocal microscopy image following expansion of membrane labeled Brainbow3.0 neurons from boxed region in (e). (g) Pre-expansion confocal image showing one optical section of boxed region in (f). (h) Post-expansion image of (g). Scale bars: (a) 100 µm, (b) 100 µm (physical size post-expansion, 413 µm); (c) 300 µm×254 µm×25 µm, (c) (i) 1 µm, (d) 500 µm, (e) 500 µm (1980 µm); (f) 5 µm, (g) 5 µm (19.8 µm); (h) 50 µm (198 µm).
Figure 6B:
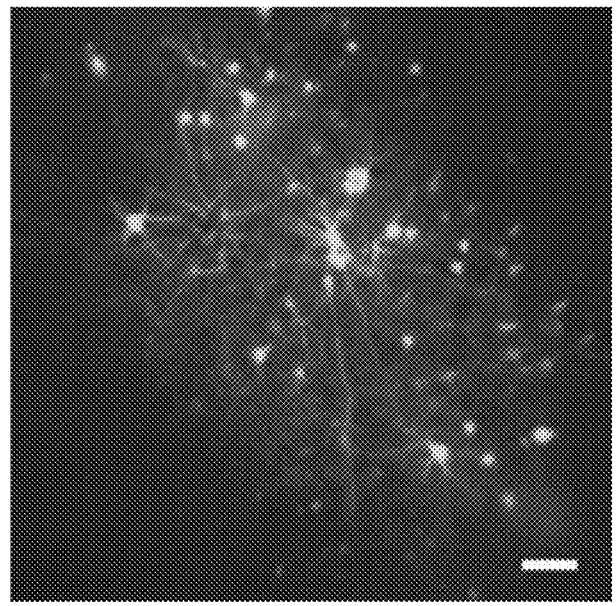
Figure 6C:
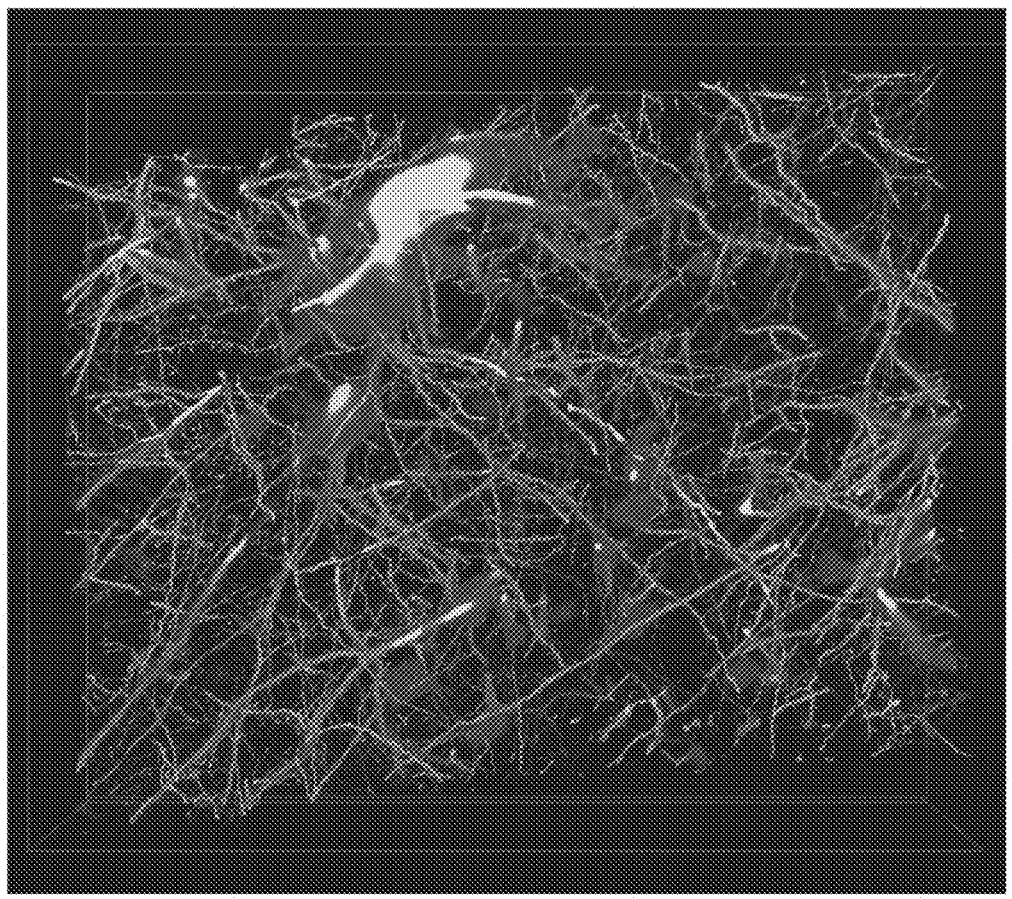
Figure 6D:
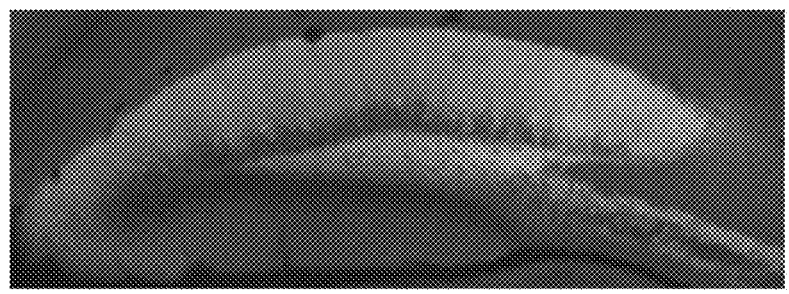
Figure 6E:
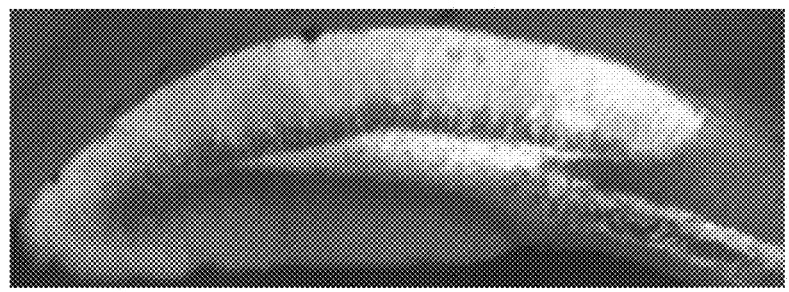
Figure 6F:
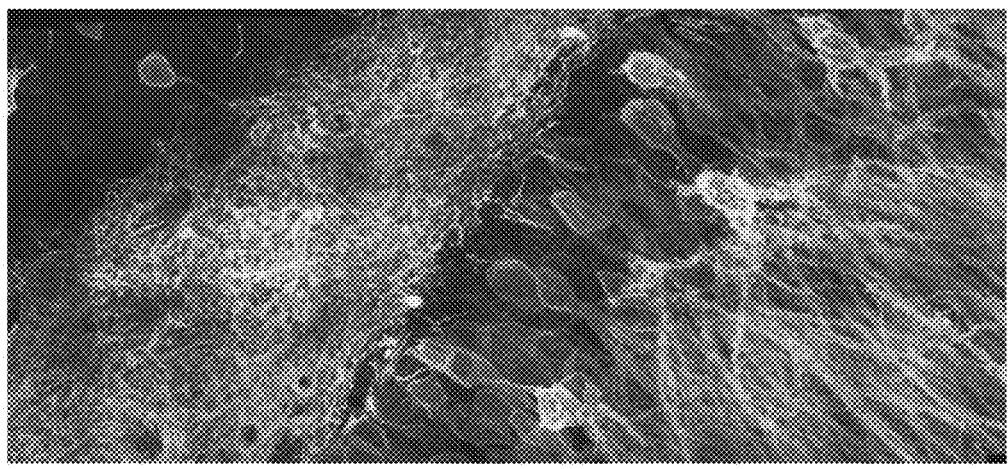
Figure 6G:
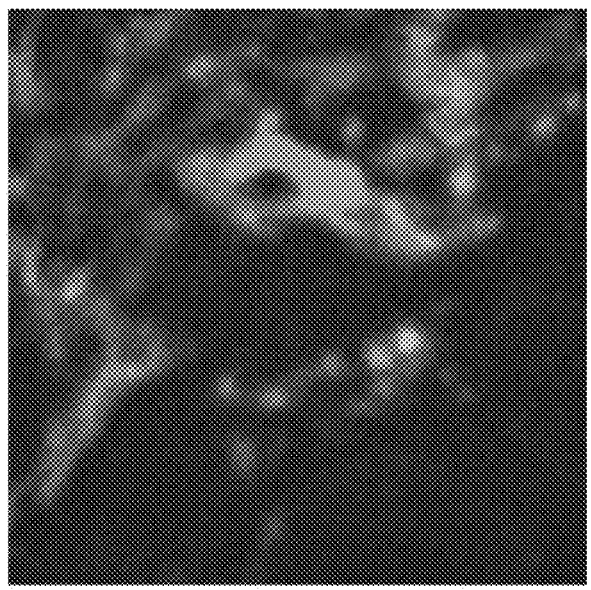
Figure 6H:
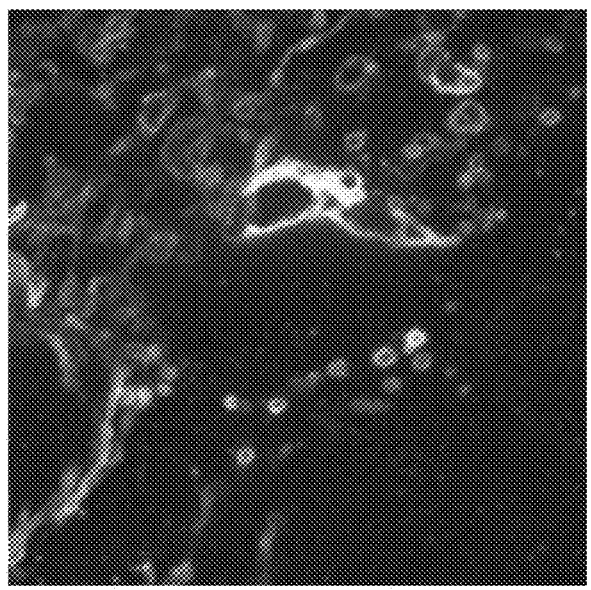

Transgenic animals expressing FPs, as well as animals expressing FPs after viral gene delivery, are routinely used in biology for labeling proteins and cells in intact tissues and organisms. proExM was used for the visualization of FPs expressed in intact mammalian brain tissue, including the brains of mice (FIG. 15) and a rhesus macaque (FIG. 6a-c), obtaining images that showed minimal macroscale distortion after expansion (e.g., compare FIG. 6a vs 6b). Using a high magnification lens on a conventional confocal microscope, dendritic spine morphology was easily resolved after expansion, with even thin spine necks visible (FIG. 6c inset, arrow).

proExM was used for imaging of mouse brain circuitry expressing virally delivered Brainbow3.0[13,14], which marks neurons with random combinations of membrane anchored FPs. These FPs are antigenically distinct to allow for subsequent amplification via antibodies. Following proExM, antibody staining and morphology are preserved in brain tissues (FIG. 6d vs 6e). Confocal imaging allows for large volume, multi-color super-resolved imaging of the Brainbow sample (FIG. 6f). Side-by-side comparison of confocal images before (FIG. 6g) and after (FIG. 6h) expansion shows how axons and dendrites too close to resolve before expansion can be clearly resolved after expansion (FIG. 6g, h).

Fluorescent proteins and fluorescent antibodies delivered using standard methods are also retained in the gel, and furthermore exhibit fluorescent signals following nonspecific proteolysis treatment. The multi-color, large volume capability of proExM was demonstrated by expanding Brainbow samples, which may be useful for circuit mapping. Preservation of endogenous fluorescence allows for the use of transgenic animals, viral expression vectors, and transfection of FPs, all without immunostaining.

Samples processed with proExM are optically clear and index matched to water[1]. This allows for super-resolution imaging deep into samples, on conventional fluorescence microscopes, limited only by working distance of the objective lens.

In one embodiment the present invention provides for the anchoring proteins into the swellable gel of Expansion Microscopy (ExM), followed by a more mild disruption treatment that minimizes damage to the individual proteins, allowing staining and other treatments on the proteins to be carried out after expansion.

In contrast to the previously described ExM method, wherein all staining must be carried out before expansion, in the native intact tissue state, the present invention allows staining to be carried out in the expanded state, with the native proteins transferred into the quasi-in vitro environment of the expanded gel. Without wishing to be bound to any particular theory, it is believed that this simplified chemical environment alleviates many issues that place limitations on biological staining methods including steric hindrance and diffusional access, and potentially also autofluorescence and non-specific binding. Thus, rapid staining of thick tissue specimens, higher staining intensity, and potentially better staining of challenging targets is provided with less optimization than is required with current staining methods. The present invention also enables the use of probes that would not be compatible with the native tissue environment, among other potential applications.

In one embodiment, the invention provides the use of a chemical to anchor proteins directly to any swellable material as described in International patent application serial number PCT/US15/16788. In one embodiment, the chemical to anchor proteins directly to any swellable material is a succinimidyl ester of 6-((acryloyl)amino)hexanoic acid, bearing a succinimidyl ester moiety that reacts to lysine residues on proteins and an acryloyl moiety that reacts into the swellable material as it is synthesized.

In a further embodiment, the invention provides a method for tissue disruption that is designed to allow uniform expansion of the tissue-gel composite while minimally disturbing the tissue at the molecular level, in essence fragmenting and expanding the tissue rather than strongly dissolving it. In one embodiment, the invention provides the use of detergents and high temperature without enzymes, enzymes that cleave biomolecules other than proteins, enzymes that cleave proteins with greater specificity or lesser extent than proteinase K, non-aqueous solvents used in lipid extraction, and controlled chemical cleavage of proteins and other biomolecules including nucleotides, polysaccharides, and lipids, separately and in combination. This also includes strong enzymatic digestion in the case where the proteins under study are robust against this treatment.

In one embodiment, the invention provides a method for staining and other biochemical characterization of tissue in the expanded state.

As used herein, the term "sample of interest" generally refers to, but is not limited to, a biological, chemical or biochemical sample. In one embodiment, the sample of interest is a biological. A biological sample includes, but is not limited to: a tissue, a cell or any components thereof, a tumor, or all or a part of any organ including, but not limited to brain, heart, lung, liver, kidney, stomach, colon, bones, muscle, skin, glands, lymph nodes, genitals, breasts, pancreas, prostate, bladder, thyroid, and eyes.

In an embodiment, the sample of interest can be labeled or tagged preferably with a detectable label. Typically, the label or tag will bind chemically (e.g., covalently, hydrogen bonding or ionic bonding) to the sample, or a component thereof, for example, one or more proteins. The detectable label can be selective for a specific target (e.g., a biomarker or class of molecule), as can be accomplished with an antibody or other target specific binder. The detectable label preferably comprises a visible component, as is typical of a dye or fluorescent molecule; however, any signaling means used by the label is also contemplated. Contacting the sample of interest with a detectable label results in a "labeled sample of interest." A fluorescently labeled sample of interest, for example, is a sample of interest labeled through techniques such as, but not limited to, immunofluorescence, immunohistochemical or immunocytochemical staining to assist in microscopic analysis. Thus, the detectable label is preferably chemically attached to the sample of interest, or a targeted component thereof. In one embodiment, the detectable label is an antibody and/or fluorescent dye. The antibody and/or fluorescent dye, further comprises a physical, biological, or chemical anchor or moiety that attaches or crosslinks the sample to the swellable material, such as a hydrogel.

The labeled sample may furthermore include more than one label. For example, each label can have a particular or distinguishable fluorescent property, e.g., distinguishable excitation and emission wavelengths. Further, each label can have a different target specific binder that is selective for a specific and distinguishable target in, or component of, the sample.

As used herein, the term "gel" or "swellable material" are used interchangeably to generally refer to a material that expands when contacted with a liquid, such as water or other solvent. In one embodiment, the swellable material uniformly expands in three dimensions. Additionally or alternatively, the material is transparent such that, upon expansion, light can pass through the sample. In one embodiment, the swellable material is a swellable polymer or hydrogel. In one embodiment, the swellable material is formed in situ from precursors thereof. For example, one or more polymerizable materials, monomers or oligomers can be used, such as monomers selected from the group consisting of water soluble groups containing a polymerizable ethylenically unsaturated group. Monomers or oligomers can comprise one or more substituted or unsubstituted methacrylates, acrylates, acrylamides, methacrylamides, vinylalcohols, vinylamines, allylamines, allylalcohols, including divinylic crosslinkers thereof (e.g., N, N-alkylene bisacrylamides). Precursors can also comprise polymerization initiators, accelerators, inhibitors, buffers, salts, and crosslinkers.

In an embodiment, the swellable polymer is polyacrylate and copolymers or crosslinked copolymers thereof. Alternatively or additionally, the swellable material can be formed in situ by chemically crosslinking water soluble oligomers or polymers. Thus, the invention envisions adding precursors (such as water soluble precursors) of the swellable material to the sample and rendering the precursors swellable in situ.

As used herein, the terms "gelation" or "embedding" the sample in a swellable material are used interchangeably to refer to permeating (such as, perfusing, infusing, soaking, adding or other intermixing) the sample with the swellable material, preferably by adding precursors thereof. Alternatively or additionally, embedding the sample in a swellable material comprises permeating one or more monomers or other precursors throughout the sample and polymerizing and/or crosslinking the monomers or precursors to form the swellable material or polymer in situ. In this manner the sample of interest is embedded in the swellable material.

In one embodiment, a sample of interest, or a labeled sample, is permeated with a composition comprising water soluble precursors of a water swellable material and reacting the precursors to form the water swellable material in situ.

In certain embodiments, the sample of interest, or a labeled sample, can, optionally, be treated with a detergent prior to being contacted with the one or more swellable material precursors. The use of a detergent can improve the wettability of the sample or disrupt the sample to allow the one or more swellable monomer precursors to permeate throughout sample.

In one embodiment, the sample of interest is permeated with one or more monomers or a solution comprising one or more monomers or precursors which are then reacted to form a swellable or non-swellable polymerized gel depending on what step of the method is being performed. For example, if the sample of interest is to be embedded in sodium polyacrylate, a solution comprising the monomers sodium acrylate and acrylamide, and a crosslinker selected from N,N-methylenebisacrylamide (BIS), N,N'-(1,2-Dihydroxythylene)bisacrylamide), and (DHEBA) N,N'-Bis(acryloyl)cystamine (BAC), are perfused throughout the sample.

Once the sample, or labeled sample, is permeated, the solution is activated to form sodium polyacrylate or copolymer thereof. In one embodiment, the solution comprising the monomers is aqueous.

In one embodiment, one or more proteins of the sample (e.g., a labeled sample) are anchored or crosslinked to the swellable material before expansion. This can preferably be accomplished by chemically crosslinking a detectable label with the swellable material, such as during or after the polymerization or in situ formation of the swellable material.

In one embodiment, after the labeled sample has been anchored to the swellable material, the sample is, optionally, subjected to a enzymatic, chemical and/or physical disruption of the endogenous biological molecules (or the physical structure of the sample of interest, where the sample is other than a biological material), leaving the detectable labels such as fluorescent dye molecules or antibodies intact and anchored to the swellable material. In this way, the mechanical properties of the sample-swellable material complex are rendered more spatially uniform, allowing isotropic expansion with minimal artifacts.

As used herein, the terms "digestion" or "disruption of the endogenous physical structure of the sample" or the term "disruption of the endogenous biological molecules" of the sample of interest are used interchangeably and generally refer to the physical, chemical, or enzymatic digestion, disruption or break up of the sample so that it will not resist expansion.

In one embodiment, a protease enzyme is used to digest the sample-swellable material complex. It is preferable that the disruption does not impact the structure of the swellable material but disrupts the structure of the sample. Thus, the sample disruption should be substantially inert to the swellable material. The degree of digestion can be sufficient to compromise the integrity of the mechanical structure of the sample or it can be complete to the extent that the sample-swellable material complex is rendered substantially free of the sample.

In one embodiment, the physical disruption of the sample is accomplished by a more mild disruption treatment that minimizes damage to the individual proteins, allowing staining and other treatments on the proteins to be carried out after expansion. In some embodiments, such milder treatment is performed by using LyC. In some embodiments, such milder treatment is performed by autoclaving the sample.

The sample-swellable material complex is then isoptropically expanded. In one embodiment, a solvent or liquid is added to the complex which is then absorbed by the swellable material and causes swelling. In one embodiment, the liquid is water. Where the swellable material is water swellable, an aqueous solution can be used.

In one embodiment, the addition of water allows for the embedded sample to expand at least 3 times, preferably 4 times, preferably 5 times, or more its original size in three-dimensions. Thus, the sample can be increased 100-fold or more in volume. This is because the polymer is embedded throughout the sample, therefore, as the polymer swells (grows) it expands the tissue as well. Thus, the tissue sample itself becomes bigger. Surprisingly, as the material swells isotropically, the anchored tags maintain their relative spacial relationship.

The swollen material with the embedded sample of interest can be imaged on any optical microscope, allowing effective imaging of features below the classical diffraction limit. Since the resultant specimen is preferably transparent, custom microscopes capable of large volume, Widefield of view, 3D scanning may also be used in conjunction with the expanded sample. The method also provides an optional step comprising amplification of the detectable label.

As used herein, the term "ExM workflow" refers to the process of infusing a chemically fixed and permeabilized sample of interest with swellable material, which undergoes in situ polymerization (i.e., gelation), digestion of the sample-polymer composite, and expansion of the sample-polymer composite.

As used herein, the term "proExM workflow" refers to the process of anchoring proteins treatment of a fixed specimen to a swellable material (e.g., by AcX treatment), followed by gelation, digestion, expansion, and imaging.

EXAMPLES

Stock Solutions
4% Paraformaldehyde
    4% Paraformaldehyde (from Electron Microscopy Science 16% stock)
    1×PBS
Quenching Solution (Store at 4 C, can be Used Over an Extended Period of Time)
    1×PBS
    100 mM Glycine
Protein Anchoring Solution
    1×PBS
    0.1 mg/mL 6-((acryloyl)amino)hexanoic Acid, Succinimidyl Ester (Acryloyl-X, SE)
Tissue Disruption Solution (Autoclave Version)
    100 mM Tris base
    1% sodium dodecyl sulfate
    5% Triton X-100
Tissue Disruption Solution (Phospholipase Version)
    0.5×PBS
    0.1% Triton X-100
    Phospholipase A1 (Sigma, L3295) 100 U/mL
    Phospholipase D (Enzo, BML-SE301-0025) 500 U/mL
Antibody Staining Buffer (Store at 4 C, can be Used for at Least 1 Month)
    1×PBS
    0.1% Triton X-100
    2% normal donkey serum
Monomer Solution:

| Component | Stock concentration* | Amount (mL) | Final concentration* |
|---|---|---|---|
| Sodium acrylate | 38 | 2.25 | 8.6 |
| Acrylamide | 50 | 0.5 | 2.5 |
| N,N'-Methylenebisacrylamide | 2 | 0.75 | 0.15 |
| Sodium chloride | 29.2 | 4 | 11.7 |
| PBS | 10x | 1 | 1x |
| Water | | 0.9 | |
| Total | | 9.4** | |

*All concentrations in g/100 mL except PBS
**9.4/10 mL (1.06x), the remaining 6% volume brought up by initiator, accelerator and inhibitor as needed (see below).

Figure 1:
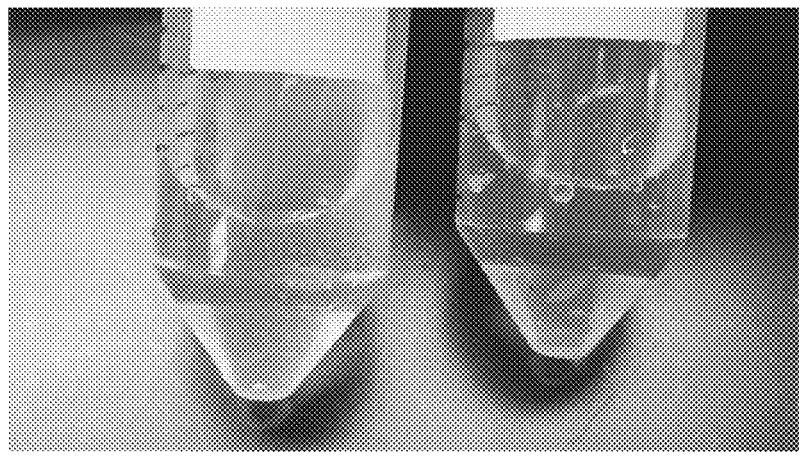
FIG. 1: 38 g/100 mL Sodium Acrylate stock solutions: correct (clear, left) and low purity (yellowish, right).

Materials and Stock Solution Storage:

Sodium acrylate sometimes comes with a variable purity level, which can affect performance. For every fresh bottle purchased, a 38 g/100 mL (33 wt %) sodium acrylate stock is made and checked to insure that it is colorless under normal room lighting. If the stock has a yellow tint (see FIG. 1), the bottle from which it was made is discarded. Once open, the sodium acrylate is stored in an airtight, low humidity, or dessicator chamber in −20 degrees C., since the solid is moisture sensitive. APS powder and 100% TEMED solution are stored in a room temperature dessicator.

The monomer solution is stored mixed up at −20 degrees C. for up to 1 month. TEMED, APS, and H-Tempo Stock solutions can be kept in −20 degrees C., and the TEMED and APS stocks is generally remade at least once every 2 weeks.

Slice Gelling Solution: Mix the following 4 solutions on ice. Monomer solutions+TEMED accelerator+APS initiator solution+4-hydroxy-TEMPO (abbreviated 4HT) inhibitor solution. The initiator solution needs to be added last, to prevent premature gelation. Solutions need to be vortexed to ensure full mixing.

Each slice needs ~200 μl of gelling solution. For 200 μl gelling solution, mix the following:
    Monomer solution (1.06×) (188 μl) (keep at 4 C to prevent premature gelation):
    Inhibitor solution (4 μl): 4-hydroxy-TEMPO (4HT stock solution at 0.5%, final concentration 0.01%) (Inhibits gelation to enable diffusion into brain slices).
    Accelerator solution (4 μl): TEMED (TEMED stock solution at 10%, final concentration 0.2% (w/w). (Accelerates radical generation by APS).
    Initiator solution (4 μl): APS (APS stock at 10%, final concentration 0.2% (w/w)). (This initiates the gelling process. This needs to be added last).

Figure 2:
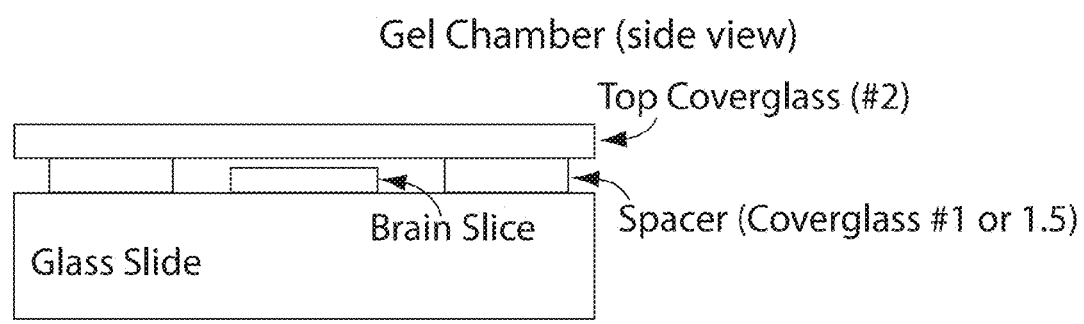
FIG. 2: is a schematic of a gel chamber.
Figure 3A:
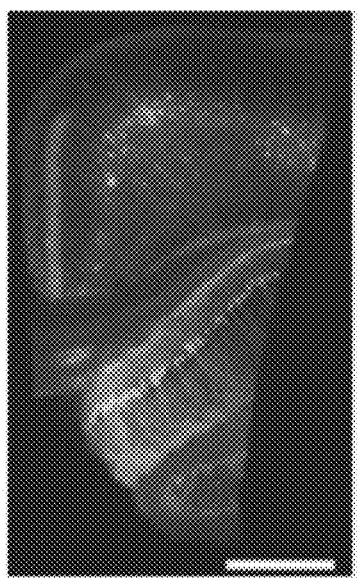
FIG. 3a-FIG. 3c: Epifluorescence images of Thy1-YFP-expressing brain tissue before (a) and after (b) expansion using autoclave version of tissue disruption protocol (green channel only). Confocal image after expansion (c). Expanded tissue was antibody stained with primary antibodies against green fluorescent protein (GFP, green), GAD65/67 (red), and SV2 (blue). Scale bars: (a) 50 um, (b) 500 um pre-expansion (2.2 mm post-expansion), (c) 10 um pre-expansion (44 um post-expansion).
Figure 3B:
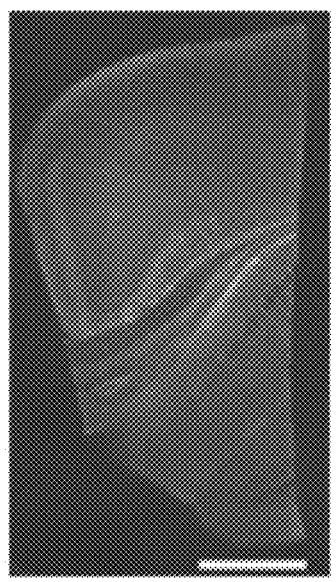
Figure 3C:
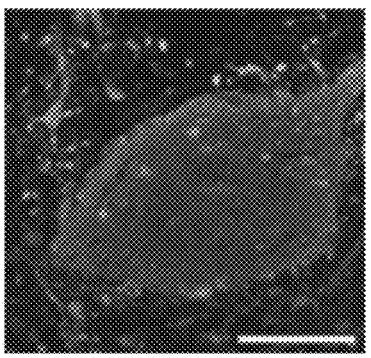

ExM Procedures for Brain Slices
Perfusion and Slicing: Essentially the same as conventional histology.
    1. Perfuse with 4% paraformaldehyde. Post-fix the brain in 4% paraformaldehyde (e.g., overnight or as needed).
    2. Quench formaldehyde fixation by incubating brain in quenching solution 1 day at 4 C.
    3. Cut brain slices on a vibratome to desired thickness.
Protein Anchoring:
    1. Wash brain slices in 1×PBS, 5 min.
    2. Incubate in protein anchoring solution, at least 12 hr at room temperature.
    3. Wash slices in 1×PBS, 5 min.
Gelling:
    1. Make sure to remove excess PBS from brain slices before incubation with gelling solution. Incubate slices in gelling solution in an Eppendorf tube for 5 mins @ 4 C, and then replace with new gelling solution for another 25 mins. Use freshly prepared gelling solution, immediately after adding APS at 4 C. (Make sure at least 100-fold excess volume of monomer solution is used. E.g., ~200 μl of gelling solution for each brain slice. Need ~100 μl for each of two incubations).
    2. Transfer slices from Eppendorf tube into a gel chamber and then incubate at 37 C for 2 hours. Gel chambers (FIG. 2) are constructed by sandwiching the slice between a slide and a coverglass, with spacers on either side of the tissue section to prevent compression of tissue slice (see schematic below). Superfrost slides (e.g. VWR 48311-703) work well as a bottom piece. Up to 100 μm sections, pieces of #1.5 coverglass can be used for spacers and for 200 μm sections, pieces of coverglasses can be stacked two coverglasses thick. (Spacers are easy to make from full coverglasses by cutting with a diamond scribe.) Make sure the slices are flat, and avoid air bubbles trapped inside the chamber.
Specimen Recovery:
    1. Gently remove top coverglass and spacers.
    2. Trim/scrape excess gel from slice using a razor blade. At this point, the slice/gel are still adhered to the bottom glass slide.
    3. Wash with 1M NaCl, 5 min.
    4. Gently remove specimen from slide with paint brush. Specimens can be stored in 1M NaCl for several days at this point.
Tissue Disruption (Choose One Version):
Autoclave Version
    1. Wash 2×15 min with Tissue Disruption Solution (autoclave version), in an autoclave-safe receptacle such as polypropylene tube.
    2. Wash once more with Tissue Disruption Solution. Treat with autoclave on liquid sterilization setting, peak temperature 121 C, hold time 60 min. For our autoclave, this treatment takes a total time of about 2 hours.

Phospholipase Version:
1. Wash 2×15 min in 1×PBS.
2. Incubate specimen in Tissue Disruption Solution (phospholipase version) at 37 C for 3 days.

Antibody Staining:
1. Move specimens into multiwall plate, with wells large enough to accommodate them after full expansion.
2. Wash 2×15 min with 0.1% Triton, then 1×15 min with Antibody Staining Buffer.
3. Incubate with primary antibodies diluted into Antibody Staining Buffer 1:200 or as desired, as in standard immunostaining protocols.
4. Wash 2×30 min with Antibody Staining Buffer.
5. Incubate with secondary antibodies diluted into Antibody Staining Buffer 1:200 or as desired, as in standard immunostaining protocols.
6. Wash 2×30 min with Antibody Staining Buffer.
7. Expand by washing thoroughly in salt-free water, e.g. wash 4×15 min in a volume of water about 200-fold greater than the original gel volume.

Image with Conventional Fluorescent, Confocal Microscope, or Other Desired Scopes As shown in FIG. 2a-FIG. 3c, epifluorescence images of Thy1-YFP-expressing brain tissue before (a) and after (b) expansion using autoclave version of tissue disruption protocol (green channel only). Confocal image after expansion (c). Expanded tissue was antibody stained with primary antibodies against green fluorescent protein (GFP, green), GAD65/67 (red), and SV2 (blue). Scale bars: (a) 50 um, (b) 500 um pre-expansion (2.2 mm post-expansion), (c) 10 um pre-expansion (44 um post-expansion).

Fluorescent Protein Screening (FIG. 4a, b). Most of the mammalian plasmids were obtained from Addgene (Table 1 and 3). To construct the remaining ones, pmKate2-H2B-N1 and pPATagRFP-H2B-N1 plasmids the respective genes were PCR amplified as AgeI/NotI fragments and swapped with the LSSmOrange gene in pH2B-LSSmOrange-N1 (Addgene). To generate NLS-iRFP fusion protein, a PCR-amplified AgeI/NotI fragment encoding gene of iRFP was swapped with LSSmKate2 gene in pNLS-LSSmKate2-N1 (Addgene plasmid #31871). HEK293FT (Invitrogen) and HeLa (ATCC CCL-2) cells were cultured in DMEM medium (Cellgro) supplemented with 10% FBS (Invitrogen), 1% penicillin/streptomycin (Cellgro), and 1% sodium pyruvate (BioWhittaker). HEK293FT and HeLa cells were used for ease of transfection, cell lines were authenticated by STR-profiling and checked for *mycoplasma* contamination by the manufacturer. Cells were transfected using TransIT-X2 transfection reagent (Mirus Bio) according to the manufacturer's protocol. Wide-field imaging of live HEK293FT cells was performed 24 h after transfection using a Nikon Eclipse Ti inverted microscope equipped with 10×NA 0.3 objective lens, a SPECTRA X light engine (Lumencor) with 390/22 nm, 438/24 nm, 475/28 nm, 510/25 nm, 585/29 nm, and 631/28 nm exciters (Semrock), and a 5.5 Zyla camera (Andor), controlled by NIS-Elements AR software. Immediately after live cell imaging cell cultures were fixed with 4% paraformaldehyde for 10 min, and permeabilized with 0.1% Triton-X for 15 min, washed 3 times for 5 minutes with PBS (Cellgro) and treated with 0.1 mg/ml AcX (LifeTechnologies) for at least 6 h, gelled and digested with proteinase K overnight as described below (see "AcX treatment" and "Gelation, digestion and expansion" sections).

Following digestion, the samples were processed by extensively washing with PBS, and then shrunk in 1 M NaCl and 60 mm $MgCl_2$ (except for YFP, which is chloride sensitive[20], and thus was measured in the expanded state).

For control experiments shown on FIG. 12 gels were washed only with PBS. Registration of pre- and post-sample processing images was carried out with an implementation of the SIFT/RANSAC algorithm, in MATLAB. Automatic Otsu thresholding via CellProfiler[21] of fluorescent nuclei allowed for automated measurement of fluorescent intensity in the same set of cells before and after sample processing. Intensity measurements for each nucleus before and after sample processing were normalized by segmented area to account for fluorophore dilution (area was used since epifluorescent optical sectioning mitigates the axial expansion effect on brightness).

Quantification of fluorescent dye retention during ProExM. Fluorescent secondary antibodies (goat anti-rabbit, 10 µg/mL) were purchased from commercial vendors (see Table 2 for list of fluorescent secondary antibodies). Retention (FIG. 4c) was quantified via before-after proExM imaging mouse cortex as described below. Cortical sections of wild type (only used for Alexa 488 due to Thy1-YFP crosstalk) and Thy1-YFP brain slices (50 µm thick) were stained with anti-Homer primary antibody (Synaptic Systems; see Table 4), and different secondary antibodies described in Table 2.

TABLE 4

Primary antibodies used.

| Target | Host | Clonality | Manufacturer | Catalog No. |
|---|---|---|---|---|
| GFP | chicken | poly | Abcam | ab13970 |
| GFP | rabbit | poly | Life Technologies | A11122 |
| bassoon | mouse | mono | Abcam | ab82958 |
| homer | rabbit | mono | Abcam | ab184955 |
| homer | rabbit | poly | Synaptic Systems | 160 003 |
| lamin A/C | mouse | mono | Cell Signaling Technologies | 4777S |
| TOM20 | rabbit | poly | Santa Cruz Biotech | sc-11415 |
| post-synaptic density 95 | mouse | mono | Neuromab | 73-028 |
| glutamic acid decarboxylase | rabbit | poly | Millipore | AB1511 |
| myelin basic protein | rabbit | poly | Abcam | ab40390 |
| vimentin | chicken | poly | Abcam | ab24525 |
| glial fibrillary acid protein | mouse | mono | Santa Cruz Biotech | sc-166458 |

Epifluorescence images of brain slices were taken with 4×0.13 NA objective pre-gelation. Following proExM gelation and digestion, the brain slices were washed extensively with PBS (3×30 min), and epifluorescence images of the slice were taken again with identical imaging conditions. A region of interest in the cortex was used to determine the loss of fluorescence during proExM processing. Intensity measurements before and after sample processing were normalized by segmented area to account for fluorophore dilution.

Structured illumination microscopy pre-expansion imaging. HeLa cells were fixed with 4% paraformaldehyde for 10 min, washed 3 times for 5 minutes with PBS, and permeabilized with 0.1% Triton-X for 15 min. Microtubules in fixed HeLa were stained with primary antibodies (Sheep Anti-Tubulin, Cytoskeleton ATNO2) in blocking buffer 1×PBS with 0.1% Triton X-100 and 2% normal donkey serum (PBT) at a concentration of 10 µg/mL for 1-4 hours and then washed in PBS three times for 5 minutes each. Specimens were then incubated with secondary antibodies (Donkey Anti-Sheep Alexa 488, Life Technologies, 10 µg/mL) in PBT for 1-4 hours and then washed in PBS three times for 5 minutes. 50 µm brain tissue slices were prepared and stained with primary and secondary antibodies (Rabbit Anti- Tom20, Santa Cruz Biotech sc-11415 and Goat Anti-Rabbit Alexa 568 (Life Technologies)) as described below. Super-resolution structured illumination microscope imaging was performed on a Deltavision OMX Blaze (GE healthcare) SIM microscope with 100×1.40 NA (Olympus) oil objective. Stained cells were imaged with SlowFade Gold (Invitrogen) antifade reagent for suppression of photobleaching and refractive index matching for pre-expansion imaging.

Measurement Error Quantification. The same fields of view were imaged pre- and post-expansion. Post-expansion images were first registered to the corresponding pre-expansion images by rotation, translation and uniform scaling. In case the specimen tilt changed between pre- and post-expansion imaging, this was corrected using a 3D rotation without scaling using the Fiji 3D Viewer package. These scaled images were then registered again to the pre-expansion images, but this time with a B-spline-based non-rigid registration package in Matlab[22] to capture any non-uniformities in the expansion process. Control points for registration were automatically generated using scale-invariant feature transform (SIFT) keypoints[23]. SIFT keypoints were generated using the VLFeat open source library[24], and random sample consensus (RANSAC) was used to estimate a geometric transformation limited to rotation, translation, and scaling. The vector deformation field mapping the scaled post-expansion image to the pre-expansion image expresses the shift of each point in the post-expansion image relative to an ideal uniform expansion. By subtracting the resulting vectors at any two points, the relative localization error was determined using the post-expansion image to measure the distance between those two points. The entire population of possible point-to-point measurements was sampled to determine the root-mean-square error for such measurements as a function of measurement length.

Brainbow3.0 injection and antibody staining. Brainbow3.0 rAAV (University of Pennsylvania, Penn Vector Core) injections were performed as previously described [13]. Briefly, transgenic mice were anesthetized continuously with isoflurane and head-fixed to a stereotaxic apparatus. Surgery took place under sterile conditions with the animal lying on a heating pad. 2 μL AAV mix (7.5×10$^{12}$ genome copy/mL) was injected at a rate of 0.2 μl/min through a 34-gauge injection needle into the brain (e.g., cortex, hippocampus), after which the needle was allowed to rest at the injection site for 5 min to allow viral diffusion. Animals expressed virus for 3-4 weeks, then were perfused (see "Mouse perfusion").

Primary antibodies against Brainbow 3.0 fluorophores (chicken anti-GFP, guinea-pig anti-mKate2, rat anti-mTFP) were produced by the Cai lab. Slices were permeabilized and blocked with 1×PBS with 0.1% Triton X-100 and 2% normal donkey serum (PBT) for 30 minutes before antibody staining (all incubations at room temperature (RT)). Slices were incubated with primary antibodies for 3 days at 4° C. in PBT, and then washed four times 30 minutes with PBT. Slices were incubated with secondary antibodies for 1 day at RT. Secondary antibodies used were: goat Anti-Chicken Alexa 488, goat Anti-Rat Alexa 546 (Life Technologies) and donkey Anti-Guinea Pig CF633 (Biotium), all at 10 μg/mL.

Mouse perfusion. All solutions below were made up in 1× phosphate buffered saline (PBS). Mice were anesthetized with isoflurane and perfused transcardially with ice cold 4% paraformaldehyde. Brains were dissected out, left in 4% paraformaldehyde at 4° C. for one day, before moving to 100 mM glycine. Slices (50 μm, and 100 μm) were sliced on a vibratome (Leica VT1000S) and stored at 4° C. until staining.

AcX treatment. Acryloyl-X, SE (6-((acryloyl)amino) hexanoic acid, succinimidyl ester, here abbreviated AcX; Thermo-Fisher) was resuspended in anhydrous DMSO at a concentration of 10 mg/mL, aliquoted and stored frozen in a desiccated environment. AcX prepared this way can be stored for up to 2 months. For anchoring, cells and tissue slices are incubated in AcX diluted in PBS at a concentration of 0.1 mg/mL for >6 hours, at room temperature. For thick tissue (>100 microns), AcX penetration depth and labeling uniformity can be improved by incubating the sample at lower pH, at lower temperature, and in a 2-(N-morpholino) ethanesulfonic acid (IVIES)-based saline (100 mM MES, 150 mM NaCl; FIG. 16). Tissue slices can be incubated on a shaker or rocker to ensure mixing during the reaction.

Gelation, digestion and expansion. For AcX anchored fluorescent proteins and antibody staining, the following steps—gelation, digestion and expansion—can be performed as described previously[1]. Briefly, monomer solution (1×PBS, 2 M NaCl, 8.625% (w/w) sodium acrylate, 2.5% (w/w) acrylamide, 0.15% (w/w) N,N'-methylenebisacrylamide) was mixed, frozen in aliquots, and thawed before use. Monomer solution was cooled to 4° C. before use. Concentrated stocks (10% w/w) of ammonium persulfate (APS) initiator and tetramethylethylenediamine (TEMED) accelerator were added to the monomer solution up to 0.2% (w/w) each. For slices, the inhibitor 4-hydroxy-2,2,6,6-tetramethylpiperidin-1-oxyl (4-hydroxy-TEMPO) was added up to 0.01% (w/w) from a 0.5% (w/w) stock to inhibit gelation during diffusion of the monomer solution into tissue sections. Cells or tissue slices were incubated with the monomer solution plus APS/TEMED (and 4-hydroxy-TEMPO for slices) at 4° C. for one minute, 30 minutes for cultured cells, and brain slices respectively, and then transferred to a humidified 37° C. incubator for two hours for gelation.

Proteinase K (New England Biolabs) was diluted 1:100 to 8 units/mL in digestion buffer (50 mM Tris (pH 8), 1 mM EDTA, 0.5% Triton X-100, 1 M NaCl) and incubated with the gels fully immersed in proteinase solution overnight at RT (this step can also be performed at 37° C. for 4 hours). Digested gels were next placed in excess volumes of doubly de-ionized water for 0.25-2 hours to expand, with longer times for thicker gels. This step was repeated 3-5 times in fresh water, until the size of the expanding sample plateaued.

Fluorescence microscopy after expansion. Post-expansion confocal imaging of cells was performed on an Andor spinning disk (CSU-X1 Yokogawa) confocal system with a 60×1.40 NA oil objective (FIG. 4). To quantify expansion factor for tissue slices and low-magnification before vs. after comparisons, specimens were imaged pre-ExM on a Nikon Ti-E epifluorescence microscope with a 4×0.13 NA air objective (FIG. 5a-d, FIG. 8a-b, FIG. 10b, FIG. 12a-g, and FIGS. 15a and 15b). For FIG. 6a-b, tissue slices were imaged on Nikon Ti-E epifluorescence microscope with a 10×0.45 NA. Otherwise, all other tissues presented were imaged using an Andor spinning disk (CSU-X1 Yokogawa) confocal system with a 40×1.15 NA water immersion objective (Nikon) with the exception of FIG. 8, FIG. 10a, FIG. 11, and FIG. 13, where a Zeiss LSM 710 with 40×1.1 NA water objective. The Zeiss LSM 710 with 10×0.3 NA air lens was used.

To stabilize the gels against drift during imaging following expansion, gels were placed in glass bottom 6 well plates with all excess liquid removed. If needed for immobilization, liquid low melt agarose (2% w/w) was pipetted around the gel and allowed to solidify, to encase the gels before imaging.

PALM imaging. PALM data was recorded on a custom-built three-camera RAMM frame microscope (ASI) using an Olympus 1.4 NA PLAPON 60× OSC objective, and a custom tube lens (LAO-300.0, Melles Griot), resulting in 100× overall magnification[25]. A 2 mm thick quad-band excitation dichroic (ZT405/488/561/640rpc, Chroma), a 2 mm thick emission dichroic (T560lpxr, Chroma), and a band-pass emission filter (FF01-609/54-25, Semrock) filtered the emitted light. Dendra2 was photoconverted by 100 µs long excitation pulses of 405 nm (50 W/cm$^2$) every 200 ms, which was ramped up to 1.2 ms long pulses every 200 ms during the course of image acquisition. Stroboscopic 405-nm excitation of the Stradus 405-100 laser (Vortran) was achieved using a NI-DAQ-USB-6363 acquisition board (National Instruments), Photoconverted Dendra2 molecules were excited with a 555-nm DPSS laser (CrystaLaser) at estimated sample power levels of 2 kW/cm$^2$. Fluorescence was detected using µManager (v. 1.4.20)[26] with a back-illuminated EMCCD camera (Andor Technology, Ixon Ultra DU-897 –BV, 17 MHz EM amplifier, Gain 500, full-chip) at 20 frames/s.

Particle localization. Localizer[27] was used for 8-way adjacency particle detection with 20 GLRT sensitivity and a PSF of 1.3 pixels. The resulting particles were drift corrected using ad-hoc fiducial markers. For each detected particle, integrated fluorescence intensities were converted to photon counts using analysis routines written in Igor Pro version 6.36. The mean and median localization errors were determined using equation 6 in reference[28].

ProExM of different tissue types. Standard histology preparations of mouse normal fresh frozen tissue sections, post-fixed with cold acetone, of pancreas, spleen and lung (5-10 µm) were obtained from US Biomax (MOFTS036, MOFTS051, and MOFTS031, respectively). Tissues were blocked with 1×PBS with 0.1% Triton X-100 and 2% normal donkey serum (PBT) for 30 minutes before antibody staining. Tissues were stained with primary chicken anti-vimentin (Abcam) for 4 hours at RT and then washed four times 30 minutes with PBT. Slices were incubated with secondary antibodies for 2 hours at RT (Anti-Chicken Alexa 488, Life Technologies). Pre-expansion imaging was performed as described above. Tissues were incubated with 0.05 mg/mL AcX in PBS at RT overnight before gelation, digestion and expansion described above with the exception that digestion was performed at 60° C. for 4 hours.

Antibody staining of endogenous proteins. Specimens, either before gelation or after autoclave or LysC treatment, were incubated in 1×PBS with 0.1% Triton X-100 and 2% normal donkey serum (PBT) at room temperature (RT) for 2 hours for blocking, and in the case of pre-gelation specimens, permeabilization. Specimens were incubated with primary antibodies at 3 µg/mL in PBT, for 4 hours (RT), and then washed four times 30 minutes with PBT. Specimens were incubated with secondary antibodies at 20 µg/mL in PBT, for 4 hours (RT), and then washed four times at least 30 minutes with PBT. Secondary antibodies used were: goat Anti-Chicken Alexa 488 (Life Technologies), goat Anti-Rabbit Alexa 546 (Life Technologies) and goat Anti-Mouse CF633 (Biotium), except that goat Anti-Chicken Alexa 546 (Life Technologies) was used for FIG. 8e, g(ii), h(ii) and goat Anti-Rabbit Alexa 488 (Life Technologies) was used for FIG. 4e.

Specimen disruption using autoclave. After gelation, gels were recovered from gelation chambers and washed in 1M NaCl. Gels were washed for 15 minutes in Disruption Buffer (100 mM Tris base, 5% Triton X-100, 1% SDS), then placed in fresh Disruption Buffer and treated by autoclave on liquid sterilization mode with a temperature of 121° C. held for one hour. This treatment must be carried out in an autoclave-safe vessel such as polypropylene tubes. Gels were then transferred to well plates for antibody staining and imaging and washed in PBT (1×PBS, 2% normal donkey serum, 0.1% Triton X-100) to remove Disruption Buffer.

Mild digestion with LysC. After gelation, gels were pre-treated in HBSS buffer (with calcium and magnesium, ThermoFisher Scientific) with 600 U/ml collagenase type II (Life Technologies) in 37° C. for 2-4 hours. Gels were then washed for 5 minutes in LysC digestion buffer (25 mM Tris-HCl, 1 mM EDTA, pH 8.5) and incubated with 33 µg/ml LysC (Promega) in 37° C. for at least 8 hours. Finally, gels were washed in LysC digestion buffer 3× for 30 mins each and were subjected to immunostaining with identical steps that have been described above.

Synthesis of SNOTRAP-biotin. To a stirred 2-(diphenylphosphino)-benzenethiol (100 mg, 0.34 mmol) in dry DMF (5 mL) was added biotin-PEGS-propionic acid (100 mg, 0.22 mmol, ChemPep, Inc), N,N'-dicyclohexylcarbodiimide (DCC) (70 mg, 0.34 mmol) and dimethylaminopyridine (DMAP) (4 mg, 0.03 mmol) successively. The resulting mixture was stirred for 7 h at room temperature, and the resulting clear solution then concentrated under reduced pressure and purified by flash chromatography (hexane/EtOAc/MeOH gradient) to give the desired product (yield 30%). The SNOTRAP probe was repurified on an 1100 HPLC system with a photodiode array UV detector at 254 nm (Agilent Technologies, Wilmington, Del.). HPLC columns and solvent systems were as follows: a semi-preparative Phenomenex Luna C18 (25 cm×9.4 mm, 10 µm) column was eluted with a linear gradient of 0.1% formic acid in water (A) and acetonitrile (B) at a flow rate of 2.5 mL/min. Solvent composition was initially at 40% for 5 min, 70% at 10 min, 90% at 20 min, and then further to 95% B over 8 min. $^1$H NMR (500 MHz, CD$_3$CN, δ) 7.42-7.38 (m, 9H), 7.23-7.18 (m, 4H), 7.84 (m, 1H), 4.60-4.51 (m, 2H), 3.67-3.51 (m, 12H), 3.2 (m, 3H), 2.8 (m, 2H), 2.55 (t, 2H), 2.15 (t, 2H), 1.57-3.51 (m, 6H); $^{13}$C NMR (125 MHz, CD$_3$CN, δ) 199.19, 172.5, 164.5, 144.8, 138.1, 137.0, 134.8, 129.9, 129.6, 129.6, 118.3, 69.2, 63.1, 62.3, 45.9, 42.5, 38.2, 27.1, 23.1, 22.5; $^{31}$P NMR (202 MHz, CD$_3$CN, δ) −10.3; HRMS-ESI$^+$ (m/z): [M+H$^+$]$^+$ calculated for C$_{37}$H$_{47}$N$_3$O$_6$PS$_2$, 724.2638; found, 724.2632.

ProExM of SNOTRAP staining. For SNOTRAP staining, primary neuron culture were washed 3×5 minutes using PBS and fixed using cold methanol at −20° C. for 15 minutes. Neurons were incubated with 300 nM N-ethylmaleimide (NEM) (Thermo Scientific) in PBS-Triton X100 (0.3% v/v) at 37° C. for 30 minutes to block the free —SH group on proteins. Cells were then washed 3×5 minutes using PBS and incubated with SNOTRAP probe (250 uM) in acetonitrile-PBS-triton (50%: 50% v/v) at R.T. for 1 hour, and then further incubated with streptavidin-Alexa 488 (Thermo Scientific) in 1/500 dilution (PBS-Triton) at R.T. for 1 hour and afterwards washed 5×5 minutes. Antibody staining for anti-tubulin (Alexa 546 secondary) and proExM was performed as described above.

Animal care. All methods for animal care and use were approved by the Massachusetts Institute of Technology Committee on Animal Care and were in accordance with the National Institutes of Health Guide for the Care and Use of Laboratory Animals. One adult male rhesus macaque (*Macaca mulatta*) weighing 12 kg was used for this study, as well as 1 C57BL/6 mouse, 4 Emx1-Cre mice, and 10 Thy1-YFP mice, ages ~1-3 months old. Mice were used without regard for gender.

Macaque procedures. Virus injections were performed with sevoflurane anesthesia using stereotactic coordinates to target 8 injection sites. Viruses (AAV8,) were centrifuged and loaded into 10 μL gas-tight syringes (Hamilton) that had been back-filled. with silicone oil (Sigma). A total of 3 μL of virus was infused into the brain at two locations (deep then 500 μm superficial) at a rate of 100-200 nL/minute using stereotactic micromanipulator arms (David Kopf Instruments) and UMP3 micro-syringe injector pumps (World Precision Instruments). After each injection, the needle and syringe were left in place for 10 minutes before withdrawal. Blunt 33G needles were used for all injections. 1 mg Dexamethasone was also administered to prevent brain swelling. Euthanasia took place 4 weeks after viral injection. An overdose of pentobarbital was administered prior to perfusion with phosphate buffered saline (PBS) and 4% paraformaldehyde (PFA). The brain was then extracted, blocked, and stored in a 20% glycerol with 0.1% sodium azide solution, and finally cut into 40 μm microtome sections.

While this invention has been particularly shown and described with references to preferred embodiments thereof, it will be understood by those skilled in the art that various changes in form and details may be made therein without departing from the scope of the invention encompassed by the appended claims.

REFERENCES

1. Chen, F., Tillberg, P. W. & Boyden, E. S. Expansion microscopy. *Science* (80-.). 347, 543-548 (2015).
2. Laemmli, U. K. Cleavage of structural proteins during the assembly of the head of bacteriophage T4. *Nature* 227, 680-685 (1970).
3. N C A Hunt B Jasani, R. A. High temperature antigen retrieval and loss of nuclear morphology: a comparison of microwave\rand autoclave techniques. *J. Clin. Pathol.* 49, 767-770 (1996).
4. Jekel, P. A., Weijer, W. J. & Beintema, J. J. Use of endoproteinase Lys-C from Lysobacter enzymogenes in protein sequence analysis. *Anal. Biochem.* 134, 347-354 (1983).
5. Wu, C. C., MacCoss, M. J., Howell, K. E. & Yates, J. R. A method for the comprehensive proteomic analysis of membrane proteins. *Nat. Biotechnol.* 21, 532-8 (2003).
6. Sniegowski, J. A., Phail, M. E. & Wachter, R. M. Maturation efficiency, trypsin sensitivity, and optical properties of Arg96, Glu222, and Gly67 variants of green fluorescent protein. *Biochem. Biophys. Res. Commun.* 332, 657-63 (2005).
7. Bokman, S. H. & Ward, W. W. Renaturation of Aequorea gree-fluorescent protein. *Biochem. Biophys. Res. Commun.* 101, 1372-80 (1981).
8. Seneviratne, U. et al. S-nitrosation of proteins relevant to Alzheimer's disease during early stages of neurodegeneration. *Proc. Natl. Acad. Sci. U.S.A* 1521318113-(2016). doi:10.1073/pnas.1521318113
9. Huang, B., Jones, S. A., Brandenburg, B. & Zhuang, X. Whole-cell 3D STORM reveals interactions between cellular structures with nanometer-scale resolution. *Nat. Methods* 5, 1047-1052 (2008).
10. Rego, E. H. et al. Nonlinear structured-illumination microscopy with a photoswitchable protein reveals cellular structures at 50-nm resolution. *Proc. Natl. Acad. Sci. U.S.A* 109, E135-43 (2012).
11. Bates, M., Huang, B., Dempsey, G. T. & Zhuang, X. Multicolor super-resolution imaging with photo-switchable fluorescent probes. *Science* 317, 1749-1753 (2007).
12. Bossi, M. et al. Multicolor far-field fluorescence nanoscopy through isolated detection of distinct molecular species. *Nano Lett.* 8, 2463-8 (2008).
13. Cai, D., Cohen, K. B., Luo, T., Lichtman, J. W. & Sanes, J. R. Improved tools for the Brainbow toolbox. *Nat. Methods* 10, 540-7 (2013).
14. Livet, J. et al. Transgenic strategies for combinatorial expression of fluorescent proteins in the nervous system. *Nature* 450, 56-62 (2007).
15. Schnell, U., Dijk, F., Sjollema, K. A. & Giepmans, B. N. G. Immunolabeling artifacts and the need for live-cell imaging. *Nat. Methods* 9, 152-158 (2012).
16. Hackstadt, T. Steric hindrance of antibody binding to surface proteins of *Coxiella burnetti* by phase I lipopolysaccharide. *Infect Immun* 56, 802-807 (1988).
17. Jiménez, N. & Post, J. A. A Novel Approach for Intracellular 3D Immuno-Labeling for Electron Tomography. *Traffic* 13, 926-933 (2012).
18. Randall, K. J. & Pearse, G. A dual-label technique for the immunohistochemical demonstration of T-lymphocyte subsets in formalin-fixed, paraffin-embedded rat lymphoid tissue. *Toxicol. Pathol.* 36, 795-804 (2008).
19. Kakimoto, K., Takekoshi, S., Miyajima, K. & Osamura, R. Y. Hypothesis for the mechanism for heat-induced antigen retrieval occurring on fresh frozen sections without formalin-fixation in immunohistochemistry. *J Mol Histol* 39, 389-399 (2008).
20. Wachter, R. M. & James Remington, S. Sensitivity of the yellow variant of green fluorescent protein to halides and nitrate. *Curr. Biol.* 9, R628-R629 (1999).
21. Carpenter, A. E. et al. CellProfiler: image analysis software for identifying and quantifying cell phenotypes. *Genome Biol.* 7, R100 (2006).
22. Kroon, D.-J. B-spline Grid, Image and Point based Registration. *Matlab Cent.* at <http://www.mathworks.com/matlabcentral/fileexchange/20057-b-spline-grid-image-and-point-based-registration>
23. Lowe, D. G. Distinctive Image Features from Scale-Invariant Keypoints. *Int. J Comput. Vis.* 60, 91-110 (2004).
24. Vedaldi, A. & Fulkerson, B. Vlfeat. in *Proc. Int. Conf. Multimed.—MM '10* 1469 (ACM Press, 2010). doi:10.1145/1873951.1874249
25. English, B. P. & Singer, R. H. A three-camera imaging microscope for high-speed single-molecule tracking and super-resolution imaging in living cells. in *SPIE Nanosci.+Eng.* (Mohseni, H., Agahi, M. H. & Razeghi, M.) 955008 (International Society for Optics and Photonics, 2015). doi:10.1117/12.2190246
26. Edelstein, A., Amodaj, N., Hoover, K., Vale, R. & Stuurman, N. Computer control of microscopes using μManager. *Curr. Protoc. Mol. Biol.* Chapter 14, Unit14.20 (2010).
27. Dedecker, P., Duwé, S., Neely, R. K. & Zhang, J. Localizer: fast, accurate, open-source, and modular software package for superresolution microscopy. *J Biomed. Opt.* 17, 126008 (2012).
28. Mortensen, K. I., Churchman, L. S., Spudich, J. A. & Flyvbjerg, H. Optimized localization analysis for single-molecule tracking and super-resolution microscopy. *Nat. Methods* 7, 377-81 (2010).
29. Ai, H., Shaner, N. C., Cheng, Z., Tsien, R. Y. & Campbell, R. E. Exploration of new chromophore structures leads to the identification of improved blue fluorescent proteins. *Biochemistry* 46, 5904-10 (2007).
30. Subach, O. M., Cranfill, P. J., Davidson, M. W. & Verkhusha, V. V. An Enhanced Monomeric Blue Fluorescent Protein with the High Chemical Stability of the Chromophore. *PLoS One* 6, e28674 (2011).
31. Goedhart, J. et al. Structure-guided evolution of cyan fluorescent proteins towards a quantum yield of 93%. *Nat. Commun.* 3, 751 (2012).
32. Markwardt, M. L. et al. An improved cerulean fluorescent protein with enhanced brightness and reduced reversible photoswitching. *PLoS One* 6, e17896 (2011).
33. Heim, R., Prasher, D. C. & Tsien, R. Y. Wavelength mutations and posttranslational autoxidation of green fluorescent protein. *Proc. Natl. Acad. Sci. U.S.A* 91, 12501-4 (1994).
34. Heim, R. & Tsien, R. Y. Engineering green fluorescent protein for improved brightness, longer wavelengths and fluorescence resonance energy transfer. *Curr. Biol.* 6, 178-82 (1996).
35. Rose, R. C. & Bode, A. M. Ocular ascorbate transport and metabolism. *Comp. Biochem. Physiol. A. Comp. Physiol.* 100, 273-85 (1991).
36. Cubitt, A. B., Woollenweber, L. A. & Heim, R. Understanding structure-function relationships in the Aequorea victoria green fluorescent protein. *Methods Cell Biol.* 58, 19-30 (1999).
37. Cormack, B. P., Valdivia, R. H. & Falkow, S. FACS-optimized mutants of the green fluorescent protein (GFP). *Gene* 173, 33-8 (1996).
38. Lam, A. J. et al. Improving FRET dynamic range with bright green and red fluorescent proteins. *Nat. Methods* 9, 1005-12 (2012).
39. Ormö, M. et al. Crystal structure of the Aequorea victoria green fluorescent protein. *Science* 273, 1392-5 (1996).
40. Nagai, T. et al. A variant of yellow fluorescent protein with fast and efficient maturation for cell-biological applications. *Nat. Biotechnol.* 20, 87-90 (2002).
41. Griesbeck, O., Baird, G. S., Campbell, R. E., Zacharias, D. A. & Tsien, R. Y. Reducing the environmental sensitivity of yellow fluorescent protein. Mechanism and applications. *J Biol. Chem.* 276, 29188-94 (2001).
42. Shaner, N. C. et al. Improving the photostability of bright monomeric orange and red fluorescent proteins. *Nat. Methods* 5, 545-51 (2008).
43. Shcherbakova, D. M., Hink, M. A., Joosen, L., Gadella, T. W. J. & Verkhusha, V. V. An orange fluorescent protein with a large Stokes shift for single-excitation multicolor FCCS and FRET imaging. *J Am. Chem. Soc.* 134, 7913-23 (2012).
44. Shaner, N. C. et al. Improved monomeric red, orange and yellow fluorescent proteins derived from Discosoma sp. red fluorescent protein. *Nat. Biotechnol.* 22, 1567-72 (2004).
45. Shcherbo, D. et al. Far-red fluorescent tags for protein imaging in living tissues. *Biochem. J.* 418, 567-74 (2009).
46. Chu, J. et al. Non-invasive intravital imaging of cellular differentiation with a bright red-excitable fluorescent protein. *Nat. Methods* 11, 572-8 (2014).
47. Filonov, G. S. et al. Bright and stable near-infrared fluorescent protein for in vivo imaging. *Nat. Biotechnol.* 29, 757-61 (2011).
48. Wachter, R. M. & Remington, S. J. Sensitivity of the yellow variant of green fluorescent protein to halides and nitrate. *Curr. Biol.* 9, R628-9 (1999).
49. Gurskaya, N. G. et al. Engineering of a monomeric green-to-red photoactivatable fluorescent protein induced by blue light. *Nat. Biotechnol.* 24, 461-5 (2006).
50. McKinney, S. A., Murphy, C. S., Hazelwood, K. L., Davidson, M. W. & Looger, L. L. A bright and photostable photoconvertible fluorescent protein. *Nat. Methods* 6, 131-3 (2009).
51. Habuchi, S., Tsutsui, H., Kochaniak, A. B., Miyawaki, A. & van Oijen, A. M. mKikGR, a monomeric photoswitchable fluorescent protein. *PLoS One* 3, e3944 (2008).
52. Subach, F. V, Patterson, G. H., Renz, M., Lippincott-Schwartz, J. & Verkhusha, V. V. Bright monomeric photoactivatable red fluorescent protein for two-color super-resolution sptPALM of live cells. *J. Am. Chem. Soc.* 132, 6481-91 (2010).

What is claimed:

1. A method for the retention and imaging of proteins of a sample of interest comprising the steps of:
   (a) conjugating proteins within the sample with a bifunctional crosslinker, wherein the bifunctional crosslinker comprises a protein-reactive chemical group and a gel-reactive chemical group;
   (b) embedding the sample in a swellable material wherein proteins within the sample are anchored to the swellable material;
   (c) subjecting the sample to digestion;
   (d) swelling the swellable material to form an expanded sample;
   (e) staining the sample either before or after steps (a) (b), (c), or (d); and
   (f) imaging the expanded sample.

2. The method according to claim 1, wherein the bifunctional crosslinker is succinimidyl ester of 6-((acryloyl) amino)hexanoic acid (AcX).

3. The method according to claim 1, wherein the digestion is a physical, chemical, or enzymatic disruption of the sample.

4. The method according to claim 1, wherein the sample is subjected to antibody staining.

5. The method according to claim 4, wherein the sample is stained with one or more antibodies prior to treatment with conjugation with the bifunctional crosslinker.

6. The method according to claim 4, wherein the sample is stained with one or more antibodies after the sample is in the expanded state, and the digestion preserves protein antigenicity.

7. The method according to claim 1, wherein the sample expresses one or more fluorescent proteins.

8. The method according to claim 7, wherein the one or more fluorescent proteins are anchored to the swellable material.

9. The method according to claim 1, wherein the sample is expanded isotropically by adding water to swell the swellable material.

10. The method according to claim 3, wherein the digestion step comprises treating the sample with LysC protease, autoclaving, or proteinase K.

11. The method according to claim 3, wherein the disruption method is an enzymatic digestion.

12. The method according to claim 1, wherein embedding the biological sample in a swellable material comprises permeating the biological sample with a composition comprising precursors of a swellable polymer and forming a swellable polymer in situ.

13. The method according to claim 1, wherein the at least one protein is anchored to the swellable material.

14. A method for the retention and imaging of proteins of a sample of interest comprising the steps of:
(a) conjugating proteins within the sample with a bifunctional crosslinker, wherein the bifunctional crosslinker comprises a protein-reactive chemical group and a gel-reactive chemical group;
(b) embedding the sample in a swellable material wherein proteins within the sample are anchored to the swellable material;
(c) swelling the swellable material to form an expanded sample;
(d) staining the sample either before or after steps (a) (b), or (c); and
(e) imaging the expanded sample.

15. The method according to claim 14, wherein the bifunctional crosslinker is succinimidyl ester of 6-((acryloyl)amino)hexanoic acid (AcX).

16. The method according to claim 14, wherein the method further comprises subjecting the sample to digestion.

17. The method according to claim 16, wherein the digestion is a physical, chemical, or enzymatic disruption of the sample.

18. The method according to claim 16, wherein the digestion preserves protein antigenicity.

19. The method according to claim 14, wherein the sample is subjected to antibody staining.

20. The method according to claim 19, wherein the sample is stained with one or more antibodies prior to treatment with conjugation with the bifunctional crosslinker.

21. The method according to claim 19, wherein the sample is stained with one or more antibodies after the sample is in the expanded state.

22. The method according to claim 14, wherein the sample expresses one or more fluorescent proteins.

23. The method according to claim 22, wherein the one or more fluorescent proteins are anchored to the swellable material.

24. The method according to claim 14, wherein the sample is expanded isotropically by adding water to swell the swellable material.

25. The method according to claim 17, wherein the digestion step comprises treating the sample with LysC protease, autoclaving, or proteinase K.

26. The method according to claim 17, wherein the disruption method is an enzymatic digestion.

27. The method according to claim 1, wherein embedding the biological sample in a swellable material comprises permeating the biological sample with a composition comprising precursors of a swellable polymer and forming a swellable polymer in situ.

* * * * *

UNITED STATES PATENT AND TRADEMARK OFFICE
CERTIFICATE OF CORRECTION

PATENT NO. : 10,317,321 B2
APPLICATION NO. : 15/229545
DATED : June 11, 2019
INVENTOR(S) : Paul Warren Tillberg et al.

It is certified that error appears in the above-identified patent and that said Letters Patent is hereby corrected as shown below:

In the Specification

Column 1, Lines 13-18, please delete "This invention was made with government support under NYSCF-R-NI10 awarded by Hertz Foundation, NYSCF, NSF, and the Rehabilitation Institute of Chicago and 1-U01-MH106011 awarded by NIH and Cargill Fund Bioengineering Fund. The government has certain rights in the invention"

And insert:
-- "This invention was made with Government support under Grant No. R01 MH103910 and U01 MH106011 awarded by the National Institutes of Health (NIH). The Government has certain rights in the invention." --

Signed and Sealed this
Twenty-ninth Day of October, 2019

Andrei Iancu
*Director of the United States Patent and Trademark Office*